United States Patent
Back et al.

(10) Patent No.: US 11,753,379 B2
(45) Date of Patent: Sep. 12, 2023

(54) PROCESS FOR FORMING 2-HYDROXYPYRIDINE-1-OXIDE OR DERIVATIVES THEREOF

(71) Applicant: Clariant International Ltd., Muttenz (CH)

(72) Inventors: Ute Back, Blankenbach (DE); Dirk Fischer, Hahnheim (DE); Sidonie Vollrath, Frankfurt am Main (DE); Lothar Fisch, Idstein (DE); Thierry Muller, Ettelbruck (LU)

(73) Assignee: CLARIANT INTERNATIONAL LTD, Muttenz (CH)

( * ) Notice: Subject to any disclaimer, the term of this patent is extended or adjusted under 35 U.S.C. 154(b) by 0 days.

(21) Appl. No.: 17/059,144

(22) PCT Filed: May 27, 2019

(86) PCT No.: PCT/EP2019/063663
§ 371 (c)(1),
(2) Date: Nov. 25, 2020

(87) PCT Pub. No.: WO2019/228988
PCT Pub. Date: Dec. 5, 2019

(65) Prior Publication Data
US 2021/0214307 A1    Jul. 15, 2021

(30) Foreign Application Priority Data
May 30, 2018    (EP) .................................... 18175246

(51) Int. Cl.
*C07D 213/89*    (2006.01)
*C07C 215/08*    (2006.01)

(52) U.S. Cl.
CPC .......... *C07D 213/89* (2013.01); *C07C 215/08* (2013.01)

(58) Field of Classification Search
CPC ............................. C07D 213/89; C07C 215/08
See application file for complete search history.

(56) References Cited

U.S. PATENT DOCUMENTS

| | | | |
|---|---|---|---|
| 2,752,356 A * | 6/1956 | Cislak | C07D 213/89 546/290 |
| 2,809,971 A | 10/1957 | Bernstein | |
| 3,236,733 A | 2/1966 | Karsten | |
| 3,761,418 A | 9/1973 | Parran | |
| 3,972,888 A | 8/1976 | Lohaus | |
| 4,323,683 A | 4/1982 | Bolich, Jr. | |
| 4,345,080 A | 8/1982 | Bolich, Jr. | |
| 4,379,753 A | 4/1983 | Bolich, Jr. | |
| 4,470,982 A | 9/1984 | Winkler | |
| 2012/0142637 A1 | 6/2012 | Tanol | |
| 2015/0111858 A1 | 4/2015 | Tanol | |
| 2016/0095870 A1 | 4/2016 | Tanol | |

FOREIGN PATENT DOCUMENTS

| | | |
|---|---|---|
| CN | 1907971 | 2/2007 |
| CN | 105017138 | 11/2015 |
| CN | 107206012 | 9/2017 |
| DE | 2234009 | 1/1974 |

(Continued)

OTHER PUBLICATIONS

David P. Martin et al, "Exploring the Influence of the Protein Environment on Metal-Binding Pharmacophores", Journal of Medicinal Chemistry, (20140819), vol. 57, No. 16, doi:10.1021/jm500984b, ISSN 0022-2623, pp. 7126-7135, XP055498499.

(Continued)

*Primary Examiner* — Sun Jae Yoo
(74) *Attorney, Agent, or Firm* — Tod A. Waldrop

(57) ABSTRACT

A process for forming 2-hydroxypyridine-1-oxide or derivatives thereof, the process comprising inter alia providing a solution comprising at least one compound according to Formula (1)

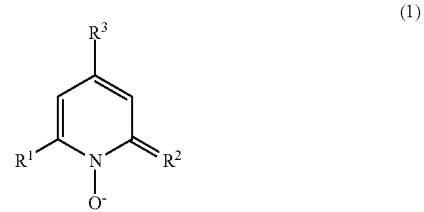

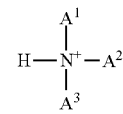

and recovering a compound according to Formula (2)

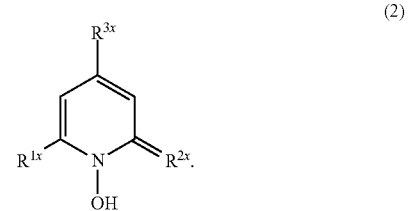

Also related products, uses, methods and compositions.

16 Claims, No Drawings

(56) References Cited

FOREIGN PATENT DOCUMENTS

| DE | 102005005009 | | 11/2005 |
|---|---|---|---|
| DE | 102010054865 | | 8/2011 |
| EP | 0550637 | | 7/1993 |
| EP | 1084696 | | 3/2001 |
| EP | 1108420 | | 6/2001 |
| GB | 1416397 | * | 3/1973 |
| WO | 9206154 | | 4/1992 |
| WO | 2013017262 | | 2/2013 |
| WO | 2013178700 | | 12/2013 |
| WO | 2015114666 | | 8/2015 |
| WO | 2016191518 | | 12/2016 |
| WO | 2018002100 | | 1/2018 |

OTHER PUBLICATIONS

E Shaw et al, "Analogs of Aspergillic Acid. IV. Substituted 2-Bromopyridine-N-oxides and Their Conversion to Cyclic Thiohydroxamic Acids", Journal of the American Chemical Society, doi:10.1021/ja01166a008, (19501001), pp. 4362-4364, URL: https://pubs.acs.org/doi/abs/10.1021/ja01166a008, (20180808), XP055498489.

H. C. Sigle et al, "In vitro investigations on the mode of action of the hydroxypyridone antimycotics rilopirox and pirocton on Candida albicans", Mycoses, GB, (20060501), vol. 49, No. 3, doi:10.1111/j.1439-0507.2006.01228.x, ISSN 0933-7407, pp. 159-168, XP055514856.

International Search Report and Written Opinion for App. No. PCT/EP2019/063663, dated Jul. 23, 2019, 14 pages.

Lohaus G et al, "Zur Chemie von antimikrobiell wirksamen 1-Hydroxy-2-pyridonen—[The chemistry of antimicrobially active 1-hydroxy-2-pyridones]", Arzneimittel Forschung. Drug Research, ECV Editio Cantor Verlag, Aulendorf, DE, (19810101), vol. 31, No. 8A, ISSN 0004-4172, pp. 1311-1316, XP009508641.

Marques do Couto, et al., "Antifungal activity of the piroctone olamine in experimental intra-abdominal candidiasis", SpringerPlus (2016), 5(1), 1-4.

* cited by examiner

PROCESS FOR FORMING 2-HYDROXYPYRIDINE-1-OXIDE OR DERIVATIVES THEREOF

FIELD OF THE INVENTION

The present invention relates to a process for forming 2-hydroxypyridine-1-oxide or derivatives thereof.

BACKGROUND OF THE INVENTION

Preservation of household formulations, such as cosmetic formulations, extends their shelf life and therefore provides greater value for money for consumers. Furthermore, preservatives prevent consumers from distributing microbes around their home or on themselves and hence provide health benefits. Anti-microbial actives are well-described in the art and there are many available that provide excellent performance. Antimicrobial actives may also have a dual function—not only to preserve the household formulation but also to effect it antimicrobial activity onto the material to which the formulation is applied. An example of this is anti-fungal substances, which not only prevent fungal growth in the (neat) formulation, but also the surface or material to which the formulation is applied e.g. hard-surfaces to be cleaned, skin, hair etc.

Examples of anti-fungal agents include ketoconazole, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine, terbinafine, zinc pyrithione, Piroctone Olamine (Octopirox®), (RS)-1-(4-chlorophenoxy)-1-imidazol-1-yl-3,3-dimethylbutan-2-one (climbazole), and combinations of the foregoing.

Piroctone Olamine, also known as Octopirox® (Clariant) and as piroctone ethanolamine, is a compound actually used in the treatment of fungal infections. The chemical name for Piroctone Olamine is the monoethanolamine salt of 1-hydroxy-4-methyl-6-(2,4,4-trimethylpentyl)-2(1H)-pyridone. Hence, Piroctone Olamine is the ethanolamine salt of the hydroxamic acid derivative piroctone.

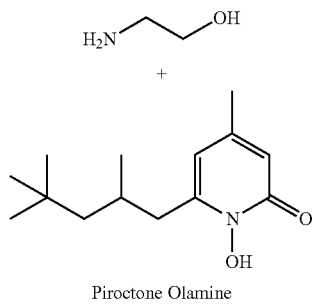

Piroctone Olamine

Piroctone Olamine is often used in anti-dandruff shampoos as a replacement for the commonly used compound zinc pyrithione. Indeed, Piroctone Olamine is known in the art for this purpose. See for example:

WO2016191518A1 (P&G): A method of improving hair quality by improving scalp health, Schwartz, James Robert; Henry, James Patrick; Kerr, Kathleen Marie; Wehmeyer, Kenneth Robert; Li, Lijuan; Mizoguchi, Haruko.

Antifungal activity of the piroctone olamine in experimental intra-abdominal candidiasis, Marques do Couto, Fabiola Maria; Carneiro do Nascimento, Silene; Junior, Silvio Francisco Pereira; Alves da Silva, Vanessa Karina; Leal, Andre Ferraz Goiana; Neves, Rejane Pereira; From SpringerPlus (2016), 5(1), 1-4.

WO2015114666A2 (Vyome Biosciences): Treatments for resistant Acne, Sengupta, Shiladitya; Chawrai, Suresh Rameshlal; Ghosh, Shamik; Ghosh, Sumana; Jain, Nilu; Sadhasivam, Suresh; Buchta, Richard; Bhattacharyya, Anamika;

DE102010054865A1 (Clariant): Use of hydroxypyridones or their salts to stabilization of hydrogen peroxide or hydrogen peroxide setting free substances; Klug, Peter; Pilz, Maurice Frederic; Back, Ute, published 2011.

DE102005005009A1 (Clariant): Preservative for cosmetics and pharmaceuticals; Klug, Peter; Klein, Sonja; Simsch, Waltraud; published 2005.

EP1108420A1 (Clariant): Cosmetic formulations containing antimicrobial Zn-octopirox; Turowski-Wanke, Angelika; Simsch, Waltraud; published 2001.

Nevertheless, there is a desire for improved preservation and anti-fungal substances. In particular, there is a desire for reducing the concentration of such substances—but this requires improved efficacy to ensure that sufficient microbial growth is are inhibited. Consumers are becoming more and more conscious of the content of household products and they desire reduced levels of 'chemicals', particularly those that may have a reputation for inhibiting cell growth. Monoethanol amine (MEA) is also not desired in view of the desire for a lower perceived risk of the presence of nitrosamines.

With the foregoing in mind, there remains a need for more efficacious preserving and anti-fungal substances, which meet present performance requirements as well as modern consumer desires and expectations.

SUMMARY OF THE INVENTION

In a first aspect, the present invention relates to a process comprising:
  (a) Providing a solution comprising:
    (i) at least one solvent, wherein the solvent is selected from the group consisting of ethanol, methanol, and mixtures thereof;
    (ii) at least one acid;
    (iii) at least one compound according to Formula (1)

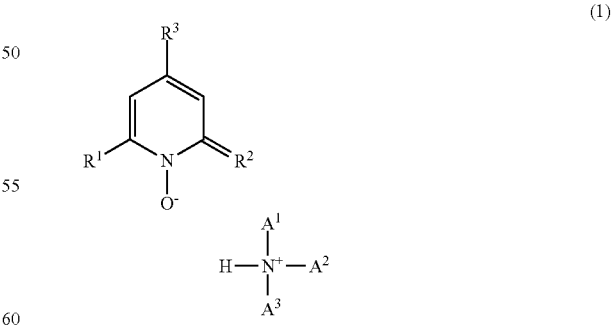

wherein
  $R^1$ is selected from the group consisting of H, a non-substituted or halogen-substituted, branched or unbranched $C_1$-$C_{20}$-alkyl radical, a non-substituted or halogen-substituted $C_5$-$C_8$-cycloalkyl radical, a non-substituted or halogen-substituted $C_6$-$C_{10}$-aryl radical or a non-substituted or halogen-substituted, branched or unbranched $C_7$-$C_{20}$-aralkyl radical;

$R^2$ is either O or S, $R^3$ is H or a branched or unbranched $C_1$-$C_4$-alkyl radical;

$A^1$ is selected from the group consisting of H, a non-substituted halogen-substituted, branched or unbranched $C_1$-$C_{20}$-alkyl radical, a non-substituted or halogen-substituted $C_5$-$C_8$-cycloalkyl radical, a branched or unbranched hydroxylated $C_1$-$C_{20}$-alkyl radical; preferably a hydroxylated $C_2$-alkyl radical;

$A^2$ is selected from the group consisting of H, a non-substituted halogen-substituted, branched or unbranched $C_1$-$C_{20}$-alkyl radical, a non-substituted or halogen-substituted $C_5$-$C_8$-cycloalkyl radical, a branched or unbranched hydroxylated $C_1$-$C_{20}$-alkyl radical; preferably a $C_2$-alkyl radical; more preferably H;

$A^3$ is selected from the group consisting of H, a non-substituted halogen-substituted, branched or unbranched $C_1$-$C_{20}$-alkyl radical, a non-substituted or halogen-substituted $C_5$-$C_8$-cycloalkyl radical, a branched or unbranched hydroxylated $C_1$-$C_{20}$-alkyl radical; preferably a $C_2$-alkyl radical; more preferably H;

(b) Heating the solution to at least 35° C.; and (c) Recovering a compound according to Formula (2)

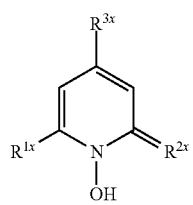

(2)

wherein $R^{1x}$ is selected from the group consisting of H, an unsubstituted or halogen-substituted, branched or unbranched $C_1$-$C_{20}$-alkyl radical, an unsubstituted or halogen-substituted $C_5$-$C_8$-cycloalkyl radical, an unsubstituted or halogen-substituted $C_6$-$C_{10}$-aryl radical or an unsubstituted or halogen-substituted, branched or unbranched $C_7$-$C_{20}$-aralkyl radical;

$R^{2x}$ is either O or S, $R^{3x}$ is H or a branched or unbranched $C_1$-$C_4$-alkyl radical.

DETAILED DESCRIPTION OF THE INVENTION

Definitions and General

In this document, including in all embodiments of all aspects of the present invention, the following definitions apply unless specifically stated otherwise. All percentages are by weight (w/w) of the total composition. All ratios are weight ratios. "wt.-%" means percentage by weight. References to 'parts' e.g. a mixture of 1 part X and 3 parts Y, is a ratio by weight. "QS" or "QSP" means sufficient quantity for 100% or for 100 g. +/− indicates the standard deviation. All ranges are inclusive and combinable. The number of significant digits conveys neither a limitation on the indicated amounts nor on the accuracy of the measurements. All numerical amounts are understood to be modified by the word "about". All measurements are understood to be made at 23° C. and at ambient conditions, where "ambient conditions" means at 1 atmosphere (atm) of pressure and at 50% relative humidity. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International. Herein "min" means "minute" or "minutes". Herein "mol" means mole. Herein "g" following a number means "gram" or "grams". "Ex." means "example". All amounts as they pertain to listed ingredients are based on the active level ('solids') and do not include carriers or by-products that may be included in commercially available materials. Herein, "comprising" means that other steps and other ingredients can be in addition. "Comprising" encompasses the terms "consisting of" and "consisting essentially of". The compositions, formulations, methods, uses, kits, and processes of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated. "In at least one embodiment" means that one or more embodiments, optionally all embodiments or a large subset of embodiments, of the present invention has/have the subsequently described feature. Where amount ranges are given, these are to be understood as being the total amount of said ingredient in the composition, or where more than one species fall within the scope of the ingredient definition, the total amount of all ingredients fitting that definition, in the composition. For example, if the composition comprises from 1% to 5% fatty alcohol, then a composition comprising 2% stearyl alcohol and 1% cetyl alcohol and no other fatty alcohol, would fall within this scope.

"Independently selected from," means that the referenced groups can be the same, different, or a mixture thereof, unless the context clearly indicates otherwise. Thus, under this definition, the phrase "X1, X2, and X3 are independently selected from noble gases" would include the scenario where X1, X2, and X3 are all the same, where X1, X2, and X3 are all different, and where X1 and X2 are the same but X3 is different.

"Molecular weight" or "M.Wt." or "MW" and grammatical equivalents mean the number average molecular weight.

"Viscosity" is measured at 25° C. using a HAAKE Rotation Viscometer VT 550 with cooling/heating vessel and sensor systems according to DIN 53019 at a shear rate of 12.9 $s^{-1}$.

"Water-soluble" refers to any material that is sufficiently soluble in water to form a clear solution to the naked eye at a concentration of 0.1% by weight of the material in water at 25° C. The term "water-insoluble" refers to any material that is not "water-soluble".

"Dry" or "substantially dry" means comprising less than 5%, less than 3% or, less than 2%, less than 1%, or about 0% of any compound or composition being in liquid form when measured at 25° C. at ambient conditions. Such compounds or compositions being in liquid form include water, oils, organic solvents and other wetting agents. "Anhydrous" means that the composition comprises less than 5%, less than 3% or, less than 2%, less than 1%, or about 0% water by total weight of the composition.

"Substantially free from" or "substantially free of" means less than 1%, or less than 0.8%, or less than 0.5%, or less than 0.3%, or about 0%, by total weight of the composition or formulation.

"Hair" means mammalian keratin fibres including scalp hair, facial hair and body hair. It includes such hair still being attached to a living subject and also hair that has been removed therefrom such as hair swatches and hair on a doll/mannequin. In at least one embodiment, "hair" means human hair. "Hair shaft" or "hair fibre" means an individual hair strand and may be used interchangeably with the term "hair."

"Cosmetically acceptable" means that the compositions, formulations or components described are suitable for use in contact with human keratinous tissue without undue toxicity, incompatibility, instability, allergic response, and the like. All compositions and formulations described herein which have the purpose of being directly applied to keratinous tissue are limited to those being cosmetically acceptable.

"Derivatives" includes but is not limited to, amide, ether, ester, amino, carboxyl, acetyl, acid, salt and/or alcohol derivatives of a given compound. In at least one embodiment, "derivatives thereof" means the amide, ether, ester, amino, carboxyl, acetyl, acid, salt and alcohol derivatives.

"Monomer" means a discrete, non-polymerised chemical moiety capable of undergoing polymerisation in the presence of an initiator or any suitable reaction that creates a macromolecule e.g. such as polycondensation, polyaddition, anionic or cationic polymerization. "Unit" means a monomer that has already been polymerised i.e. is part of a polymer.

"Polymer" means a chemical formed from the polymerisation of two or more monomers. The term "polymer" shall include all materials made by the polymerisation of monomers as well as natural polymers. Polymers made from only one type of monomer are called homopolymers. Herein, a polymer comprises at least two monomers. Polymers made from two or more different types of monomers are called copolymers. The distribution of the different monomers can be random, alternating or block-wise (i.e. block copolymer). The term "polymer" used herein includes any type of polymer including homopolymers and copolymers.

"Kit" means a package comprising a plurality of components. "Kit" may be referred to as "kit-of-parts". An example of a kit is, for example, a first composition and a separately packaged second composition and optionally application instructions.

Explanation of and Benefits Provided by the Invention

Surprisingly, it has now been found that it is possible to provide a preserving and anti-fungal agent in octoacid form i.e. pursuant to Formula (2) herein. The advantages of the octoacid form are that there is a better activity to weight ratio i.e. more efficacy per molecular weight of active. Furthermore, there is less potential for nitrosamines in the final product than for salts such as Piroctone Olamine. Furthermore, the differing solubility versus the compound according to Formula (1) e.g. Piroctone Olamine has advantages for some applications: the compound according to Formula (2) is more hydrophobic and thus more soluble in lipophilic media than Piroctone Olamine. Furthermore, the compound according to Formula (2) is more acidic and might reduce the amount of acid used for adjusting the pH in the formulation.

Without being bound by theory, it is understood that the reaction proceeds as follows: the solvent dissolves both components (the acid and the compound according to Formula (1)) and allows them to react with each other. The proton of the acid protonates the anion of the compound of Formula (1) compound leading to the octoacid form (i.e. compound according to Formula (2)). The conjugated base of the acid functions as counterion for the monoethanolammonium, keeping the latter in solution.

The present invention is inventive: indeed, it the solubility of the compound according to Formula (2) is surprising since it is normally not easy to solubilise octoacid in standard solvents. The present invention provides, for the first time, a process where the octoacid form (compound according to Formula (2)) can be isolated—previously this form could not be isolated sufficiently cleanly.

The details of the invention and its aspects are provided hereinafter.

First Aspect

The first aspect relates to a specific process as described in the SUMMARY above.

At least one embodiment of the process relates to compounds of Formula (1)

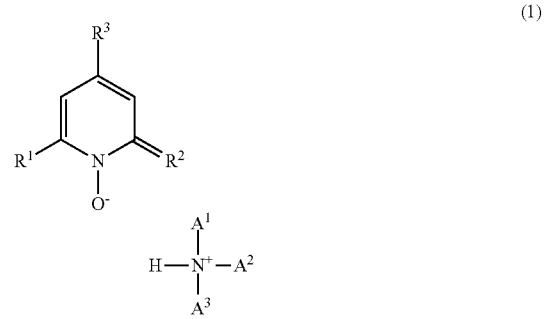

wherein $R^1$ is selected from the group consisting of H, a non-substituted or halogen-substituted, branched or unbranched $C_1$-$C_{20}$-alkyl radical, a non-substituted or halogen-substituted $C_5$-$C_8$-cycloalkyl radical, a non-substituted or halogen-substituted $C_6$-$C_{10}$-aryl radical or a non-substituted or halogen-substituted, branched or unbranched $C_7$-$C_{20}$-aralkyl radical;

$R^2$ is either O or S, $R^3$ is H or a branched or unbranched $C_1$-$C_4$-alkyl radical;

$A^1$ is selected from the group consisting of H, a non-substituted halogen-substituted, branched or unbranched $C_1$-$C_{20}$-alkyl radical, a non-substituted or halogen-substituted $C_5$-$C_8$-cycloalkyl radical, a branched or unbranched hydroxylated $C_1$-$C_{20}$-alkyl radical; preferably a hydroxylated $C_2$-alkyl radical;

$A^2$ is selected from the group consisting of H, a non-substituted halogen-substituted, branched or unbranched $C_1$-$C_{20}$-alkyl radical, a non-substituted or halogen-substituted $C_5$-$C_8$-cycloalkyl radical, a branched or unbranched hydroxylated $C_1$-$C_{20}$-alkyl radical; preferably a $C_2$-alkyl radical; more preferably H;

$A^3$ is selected from the group consisting of H, a non-substituted halogen-substituted, branched or unbranched $C_1$-$C_{20}$-alkyl radical, a non-substituted or halogen-substituted $C_5$-$C_8$-cycloalkyl radical, a branched or unbranched hydroxylated $C_1$-$C_{20}$-alkyl radical; preferably a $C_2$-alkyl radical; more preferably H.

In at least one embodiment, the radicals $R^1$ are not halogen-substituted.

In at least one embodiment, in the compound of Formula (1), $R^3$ is methyl and $R^1$ is preferably cyclohexyl or 2,4,4-trimethylpentyl.

The compounds of the Formula (1) are particularly preferably present in the form of their alkanolamine salts and especially preferably present in the form of their monoethanolamine salts or diethanolamine salts. Examples of salts of this type are mentioned in DE2234009A1 (HOECHST AG, 1974).

In a preferred embodiment, the compound according to Formula (1) is selected from the group consisting of alkanolamine salts of 4-methyl-6-(2,4,4-trimethylpentyl)-1-hydroxy-2-pyridone such as the monoethanolamine salt of 4-methyl-6-(2,4,4-trimethylpentyl)-1-hydroxy-2-pyridone (Octopirox®, Clariant), alkanolamine salts of 4-methyl-6-(cyclohexyl)-1-hydroxy-2-pyridone such as the monoethanolamine salt of 4-methyl-6-(cyclohexyl)-1-hydroxy-2-pyridone (Ciclopirox®, Sanofi-Aventis), and combinations thereof.

The compounds according to Formula (1) can be obtained in accordance with processes known from the literature, see in this regard the references given in DE2234009A1 (HOECHST AG, 1974), which is incorporated herein by reference.

In at least one embodiment, in the compound of Formula (1), $R^3$ is H and $R^1$ is H.

In at least one embodiment, $A^1$ is a branched or unbranched hydroxylated $C_1$-$C_{20}$-alkyl radical, preferably an unbranched hydroxylated $C_1$-$C_{20}$-alkyl radical. In at least one embodiment, $A^1$ is a branched or unbranched hydroxylated $C_1$-$C_4$-alkyl radical, preferably an unbranched hydroxylated $C_1$-$C_4$-alkyl radical. In at least one embodiment, $A^2$ is H, $A^3$ is H and $A^1$ is a branched or unbranched hydroxylated $C_1$-$C_4$-alkyl radical, preferably an unbranched hydroxylated $C_1$-$C_4$-alkyl radical.

At least one embodiment of the process relates to compounds of Formula (2)

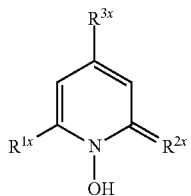

(2)

wherein
$R^{1x}$ is H, an unsubstituted or halogen-substituted, branched or unbranched $C_1$-$C_{20}$-alkyl radical, an unsubstituted or halogen-substituted $C_5$-$C_8$-cycloalkyl radical, an unsubstituted or halogen-substituted $C_6$-$C_{10}$-aryl radical or an unsubstituted or halogen-substituted, branched or unbranched $C_7$-$C_{20}$-aralkyl radical;
$R^{2x}$ is either O or S,
$R^{3x}$ is H or a branched or unbranched $C_1$-$C_4$-alkyl radical.

In at least one embodiment, in the at least one compound of Formula (2), $R^{3x}$ is H and $R^{1x}$ is H. In at least one embodiment, the compound of Formula (2) is 2-hydroxypyridine-1-oxide (also known as 2-pyridinol-1-oxide, HPNO and as 1,2-HOPO).

In a preferred embodiment, the compound according to Formula (2) is selected from the group consisting of 4-methyl-6-(2,4,4-trimethylpentyl)-1-hydroxy-2-pyridone, 4-methyl-6-(cyclohexyl)-1-hydroxy-2-pyridone and combinations thereof.

In at least one embodiment, the molar ratio of compound according to Formula (1) to acid is from 1:1 to 1:5, preferably from 1:1.5 to 1:4, more preferably from 1:2 to 1:3.

In at least one embodiment, the solution is prepared by mixing at least one compound according to Formula (1) with the at least one solvent, followed by gradually adding the at least one acid.

In at least one embodiment, during step (b), the compound according to Formula (1) is dissolved in the solution.

In at least one embodiment, the cation in Formula (1) is selected from the group consisting of monoethanolamine, diethanolamine, triethanolamine, methylamine, dimethylamine, trimethylamine, ethyl amine, diethylamine, trimethylamine, diisopropylethylamine, and combinations thereof; preferably monoethanolamine, diethanolamine, and combinations thereof.

In at least one embodiment, the acid is selected from the group consisting of hydrochloric acid, hydrobromic acid, hydroiodic acid, sulfuric acid, $HNO_3$, acetic acid, formic acid, and mixtures thereof; preferably is hydrochloric acid.

In at least one embodiment, in step (b) the solution is heated to a temperature of between 35° C. and 80° C., preferably between 40° C. between 78° C., even more preferably between 45° C. and 70° C., most preferably between 50° C. and 60° C. In at least one embodiment, in step (b) the solution is heated to a temperature of at least 35° C., preferably at least 45° C., more preferably at least 50° C., even more preferably at least 55° C. In at least one embodiment, in step (b) the solution is heated for at least 30 minutes, preferably at least 45 minutes, more preferably at least 60 minutes, even more preferably at least 75 minutes, most preferably at least 90 minutes.

In at least one embodiment, the weight ratio of compound according to Formula (1) to the solvent is from 1:0.7 to 1:1.3.

In at least one embodiment, $R^2$ and $R^{2x}$ are both O.

In at least one embodiment, $R^3$ and $R^{3x}$ are methyl and $R^1$ and $R^{1x}$ are either cyclohexyl or 2,4,4-trimethylpentyl.

In at least one embodiment, the compound according to Formula (1) is selected from the monoethanolamine salt of 4-methyl-6-(2,4,4-trimethylpentyl)-1-hydroxy-2-pyridone or the diethanolamine salt of 4-methyl-6-(2,4,4-trimethylpentyl)-1-hydroxy-2-pyridone.

In at least one embodiment, the compound according to Formula (2) is selected from the group consisting of 2-hydroxypyridine-1-oxide and 1-hydroxy-4-methyl-6-(2,4,4-trimethylpentyl)-2(1H)-pyridone.

In at least one embodiment, step (c) comprises cooling the solution; preferably comprising pouring the solution onto ice, filtering out solid material, and preferably subsequently drying the solid material. In at least one embodiment, after the solid material is filtered out, the solid material is resuspended in water and filtered out again; preferably the solid material is resuspended in water at least two times, preferably at least four times preferably at least six times. In at least one embodiment, the solid material is dried for at least six hours, preferably at least eight hours. In at least one embodiment, the solid material is in the form of cake. In at least one embodiment, the drying is carried out at a temperature of at least 80° C., preferably at least 85° C., more preferably at least 90° C., even more preferably at least 95° C., most preferably at least 99° C. In at least one embodiment, the drying is carried out in an oven. In at least one embodiment, immediately prior to step (c) the solution is at a temperature of at least 35° C., preferably at least 45° C., more preferably at least 50° C., even more preferably at least 55° C.

In at least one embodiment, the process results in a product being substantially free of Piroctone Olamine. In at least one embodiment the process results in a product being substantially free of monoethanolamine. In at least one embodiment, the process results in a product comprising less than 0.5 wt.-%, preferably less than 0.2 wt.-%, more preferably less than 0.15 wt.-% monoethanolamine. In at least one embodiment, the process results in a product being substantially free of salts of 1-hydroxypyridine-2-one compounds.

In at least one embodiment, the process results in a product having a free monoethanolamine level below 0.2% and preferably below 0.15%. In at least one embodiment, the process results in a product having a purity of at least 98.0%, preferably at least 99%. The purity can be measured by the following HPLC method: high purity RP C-18 (UV detector 210, 303 nm), gradient, buffer solution pH 2.4/acetonitrile.

In at least one embodiment, the process according results in a yield of at least 80%, preferably at least 85%, more preferably at least 90%, even more preferably at least 95%, most preferably at least 99%.

In at least one embodiment, the process results in a product having a stability at room temperature in an airtight, closed container, of at least 9 months, preferably at least 12 months, more preferably at least 15 months, even more preferably at least 18 months.

EXAMPLE EMBODIMENTS OF THE FIRST ASPECT

In a preferred embodiment, the first aspect relates to a process comprising:
(a) Providing a solution comprising:
  (i) at least one solvent, wherein the solvent is selected from the group consisting of ethanol, methanol, and mixtures thereof;
  (ii) at least one acid, preferably hydrochloric acid;
  (iii) at least one compound according to Formula (1)

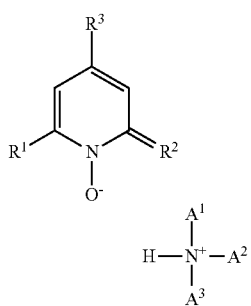

(1)

wherein
$R^1$ is selected from the group consisting of a branched or unbranched $C_1$-$C_{20}$-alkyl radicals, preferably $C_6$-$C_{10}$-alkyl radicals;
$R^2$ is either O or S,
$R^3$ is a branched or unbranched $C_1$-$C_4$-alkyl radical;
$A^1$ is selected from the group consisting of branched or unbranched hydroxylated $C_1$-$C_{20}$-alkyl radicals;
$A^2$ is H;
$A^3$ is H;

(b) Heating the solution to at least 35° C., preferably at least 45° C., more preferably at least 50° C.; and
(c) Recovering a compound according to Formula (2)

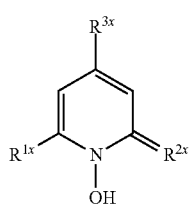

(2)

wherein
$R^{1x}$ is selected from the group consisting of branched or unbranched $C_1$-$C_{20}$-alkyl radicals, preferably $C_6$-$C_{10}$-alkyl radicals;
$R^{2x}$ is either O or S,
$R^{3x}$ is a branched or unbranched $C_1$-$C_4$-alkyl radical.

In a preferred embodiment, the first aspect relates to a process comprising:
(a) Providing a solution comprising:
  (i) at least one solvent, wherein the solvent is selected from the group consisting of ethanol, methanol, and mixtures thereof;
  (ii) at least one acid, preferably hydrochloric acid;
  (iii) at least one compound according to Formula (1)

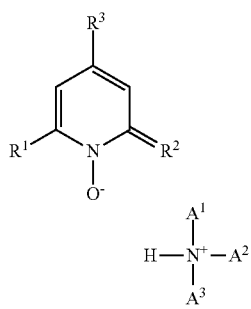

(1)

wherein
$R^1$ is selected from the group consisting of branched or unbranched $C_6$-$C_{10}$-alkyl radicals;
$R^2$ is O,
$R^3$ is H or a branched or unbranched $C_1$-$C_4$-alkyl radical;
$A^1$ is selected from the group consisting of branched or unbranched hydroxylated $C_1$-$C_{20}$-alkyl radicals;
$A^2$ is H;
$A^3$ is H;

(b) Heating the solution to at least 35° C., preferably at least 45° C., more preferably at least 50° C.; and
(c) Recovering a compound according to Formula (2)

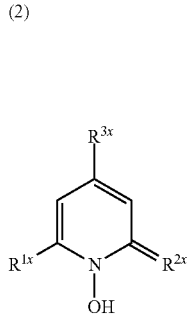

(2)

wherein
$R^{1x}$ is selected from the group consisting of branched or unbranched $C_6$-$C_{10}$-alkyl radicals;
$R^{2x}$ is O,
$R^{3x}$ is a branched or unbranched $C_1$-$C_4$-alkyl radical.

In a preferred embodiment, the first aspect relates to a process comprising:
(a) Providing a solution comprising:
  (i) at least one solvent, wherein the solvent is selected from the group consisting of ethanol, methanol, and mixtures thereof;
  (ii) at least one acid, preferably hydrochloric acid;
  (iii) at least one compound according to Formula (1)

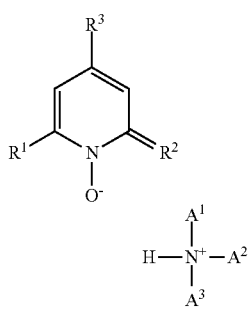

(1)

wherein
$R^1$ is a 2,4,4-trimethylpentyl-radical;
$R^2$ is O,
$R^3$ is a branched or unbranched $C_1$-$C_4$-alkyl radical, preferably methyl;
$A^1$ is selected from the group consisting of branched or unbranched hydroxylated $C_1$-$C_{20}$-alkyl radicals;
$A^2$ is H;
$A^3$ is H;

(b) Heating the solution to at least 35° C., preferably at least 45° C., more preferably at least 50° C.; and
(c) Recovering a compound according to Formula (2)

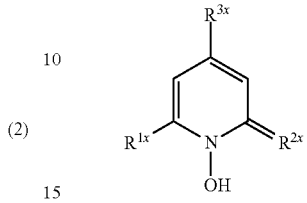

(2)

wherein
$R^{1x}$ is a 2,4,4-trimethylpentyl-radical;
$R^{2x}$ is O,
$R^{3x}$ is H or a branched or unbranched $C_1$-$C_4$-alkyl radical, preferably methyl.

Second Aspect

A second aspect relates to a product resultant from the process according to the first aspect, wherein the product preferably has a purity of at least 98.0%, more preferably at least 99%.

Preferably the product comprises a compound according to Formula (2)

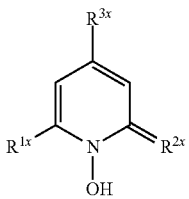

(2)

wherein
$R^{1x}$ is selected from the group consisting of H, an unsubstituted or halogen-substituted, branched or unbranched $C_1$-$C_{20}$-alkyl radical, an unsubstituted or halogen-substituted $C_5$-$C_8$-cycloalkyl radical, an unsubstituted or halogen-substituted $C_6$-$C_{10}$-aryl radical or an unsubstituted or halogen-substituted, branched or unbranched $C_7$-$C_{20}$-aralkyl radical;
$R^{2x}$ is either O or S,
$R^{3x}$ is H or a branched or unbranched $C_1$-$C_4$-alkyl radical.

In a preferred embodiment of the second aspect, the product comprises a compound according to Formula (2)

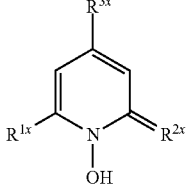

(2)

wherein
$R^{1x}$ is selected from the group consisting of H, an unsubstituted or halogen-substituted, branched or unbranched $C_1$-$C_{20}$-alkyl radical, an unsubstituted or halogen-substituted $C_5$-$C_8$-cycloalkyl radical, an unsubstituted or halogen-substituted $C_6$-$C_{10}$-aryl radical or an unsubstituted or halogen-substituted, branched or unbranched $C_7$-$C_{20}$-aralkyl radical;

$R^{2x}$ is O, $R^{3x}$ is H or a branched or unbranched $C_1$-$C_4$-alkyl radical, preferably methyl.

In a preferred embodiment of the second aspect, the product comprises a compound according to Formula (2)

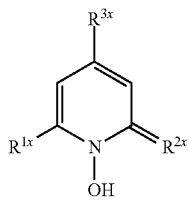

(2)

wherein $R^{1x}$ is selected from the group consisting of branched or unbranched $C_1$-$C_{20}$-alkyl radicals, preferably branched $C_6$-$C_{10}$ alkyl radicals;

$R^{2x}$ is O, $R^{3x}$ is H or a branched or unbranched $C_1$-$C_4$-alkyl radical, preferably methyl.

In a preferred embodiment of the second aspect, the product comprises a compound according to Formula (2)

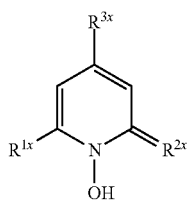

(2)

wherein $R^{1x}$ H;

$R^{2x}$ is O, $R^{3x}$ is H or a branched or unbranched $C_1$-$C_4$-alkyl radical, preferably H or methyl.

In a preferred embodiment of the second aspect, the product comprises a compound according to Formula (2)

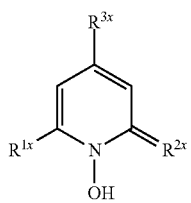

(2)

wherein $R^{1x}$ is a 2,4,4-trimethylpentyl-radical;

$R^{2x}$ is O, $R^{3x}$ is H or a branched or unbranched $C_1$-$C_4$-alkyl radical, preferably methyl.

In at least one embodiment, the product is substantially free of Piroctone Olamine. In at least one embodiment, the product is substantially free of monoethanolamine. In at least one embodiment, the product comprises less than 0.5 wt.-%, preferably less than 0.2 wt.-%, more preferably less than 0.15 wt.-% monoethanolamine. In at least one embodiment, the product is substantially free of salts of 1-hydroxy-pyridine-2-one compounds.

In at least one embodiment, the free monoethanolamine level was below 0.2% and preferably below 0.15%. In at least one embodiment, the product has a purity of at least 98.0%, preferably at least 99%. The purity can be measured by the following HPLC method: high purity RP C-18 (UV detector 210, 303 nm), gradient, buffer solution pH 2.4/acetonitrile.

In at least one embodiment, the process according to the first aspect has a yield of at least 80%, preferably at least 85%, more preferably at least 90%, even more preferably at least 95%, most preferably at least 99%.

In at least one embodiment, the product has a stability at room temperature in an air-tight, closed container, of at least 9 months, preferably at least 12 months, more preferably at least 15 months, even more preferably at least 18 months.

An alternative embodiment of the second aspect relates to product comprising a compound according to Formula (2)

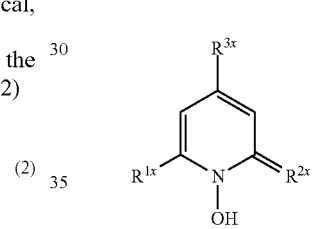

(2)

wherein $R^{1x}$ is selected from the group consisting of H, an unsubstituted or halogen-substituted, branched or unbranched $C_1$-$C_{20}$-alkyl radical, an unsubstituted or halogen-substituted $C_5$-$C_8$-cycloalkyl radical, an unsubstituted or halogen-substituted $C_6$-$C_{10}$-aryl radical or an unsubstituted or halogen-substituted, branched or unbranched $C_7$-$C_{20}$-aralkyl radical;

$R^{2x}$ is either O or S, $R^{3x}$ is H or a branched or unbranched $C_1$-$C_4$-alkyl radical;

wherein the product has a purity of at least 98.0%, preferably at least 99%.

In the alternative embodiment of the second aspect, the product may be made by any suitable process.

In a preferred alternative embodiment of the second aspect, the product comprises a compound according to Formula (2)

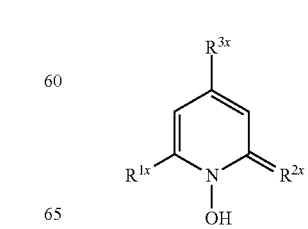

(2)

wherein $R^{1x}$ H;

$R^{2x}$ is O, $R^{3x}$ is H or a branched or unbranched $C_1$-$C_4$-alkyl radical, preferably methyl;

wherein the product has a purity of at least 98.0%, preferably at least 99%.

In a preferred alternative embodiment of the second aspect, the product comprises a compound according to Formula (2)

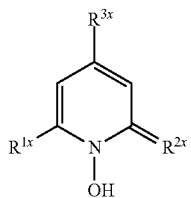

(2)

wherein $R^{1x}$ is a 2,4,4-trimethylpentyl-radical;

$R^{2x}$ is O, $R^{3x}$ is H or a branched or unbranched $C_1$-$C_4$-alkyl radical, preferably methyl; wherein the product has a purity of at least 98.0%, preferably at least 99%.

Third Aspect

A third aspect relates to the use of the product according to the second aspect for chelating metal ions. Optionally, the third aspect relates to the use of the compound according to Formula (2)

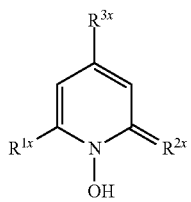

(2)

wherein $R^{1x}$ is H, an unsubstituted or halogen-substituted, branched or unbranched $C_1$-$C_{20}$-alkyl radical, an unsubstituted or halogen-substituted $C_5$-$C_8$-cycloalkyl radical, an unsubstituted or halogen-substituted $C_6$-$C_{10}$-aryl radical or an unsubstituted or halogen-substituted, branched or unbranched $C_7$-$C_{20}$-aralkyl radical;

$R^{2x}$ is either O or S, $R^{3x}$ is H or a branched or unbranched $C_1$-$C_4$-alkyl radical;

for chelating metal ions, preferably iron ions. Preferably, the use is for preserving aqueous compositions. Preferably the use is for reducing dandruff. Preferably the use is for reducing the levels of microbes.

In a preferred embodiment of the third aspect, the product comprises a compound according to Formula (2)

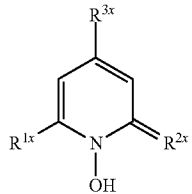

(2)

wherein $R^{1x}$ H;

$R^{2x}$ is O, $R^{3x}$ is H or a branched or unbranched $C_1$-$C_4$-alkyl radical, preferably methyl.

In a preferred embodiment of the third aspect, the product comprises a compound according to Formula (2)

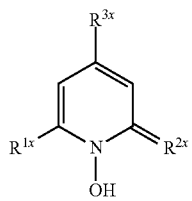

(2)

wherein $R^{1x}$ is a 2,4,4-trimethylpentyl-radical;

$R^{2x}$ is O, $R^{3x}$ is H or a branched or unbranched $C_1$-$C_4$-alkyl radical, preferably methyl.

The present invention has the advantage that the molar efficacy of the compound according to Formula (2) is equal to the efficacy of Piroctone Olamine but the mass efficacy is around 20% better for Piroctone. Without being bound by theory, the mechanism of antimicrobial activity is thought to be via the chelation of metal ions that are essential for survival of microorganisms i.e. by chelation of the metal ions, the microbes are deprived of the same. The deprotonation of Piroctone leads to exactly same active component as in Piroctone Olamine. However, it is has previously been via difficult to synthesise/isolate such compound according to Formula (2).

Fourth Aspect

A fourth aspect relates to a composition comprising the product according to the second aspect. In at least one embodiment, the composition is a cosmetic, dermatological or pharmaceutical composition.

In a preferred embodiment, the fourth aspect relates to a composition comprising a compound according to Formula (2)

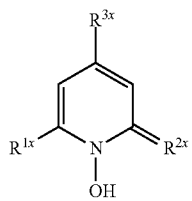

(2)

wherein
R$^{1x}$ is H, an unsubstituted or halogen-substituted, branched or unbranched C$_1$-C$_{20}$-alkyl radical, an unsubstituted or halogen-substituted C$_5$-C$_8$-cycloalkyl radical, an unsubstituted or halogen-substituted C$_6$-C$_{10}$-aryl radical or an unsubstituted or halogen-substituted, branched or unbranched C$_7$-C$_{20}$-aralkyl radical;
R$^{2x}$ is either O or S,
R$^{3x}$ is H or a branched or unbranched C$_1$-C$_4$-alkyl radical.

In a preferred embodiment of the fourth aspect, the compound is according to Formula (2)

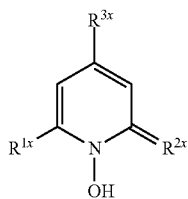

(2)

wherein
R$^{1x}$ H;
R$^{2x}$ is O,
R$^{3x}$ is H or a branched or unbranched C$_1$-C$_4$-alkyl radical, preferably methyl.

In a preferred embodiment of the third aspect, the compound is according to Formula (2)

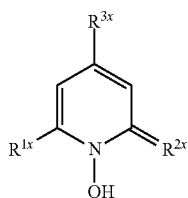

(2)

wherein
R$^{1x}$ is a 2,4,4-trimethylpentyl-radical;
R$^{2x}$ is O,
R$^{3x}$ is H or a branched or unbranched C$_1$-C$_4$-alkyl radical, preferably methyl.

In at least one embodiment, the composition is substantially free of Piroctone Olamine. In at least one embodiment, the composition is substantially free of monoethanolamine. In at least one embodiment, the composition is substantially free of salts of 1-hydroxy pyridine-2-one compounds. In at least one embodiment, the compound according to Formula (2) is added to the composition in its octoacid form.

Surfactant

In at least one embodiment, the composition comprises a surfactant. In at least one embodiment, the composition comprises a surfactant system comprising a plurality of different surfactants. In at least one embodiment, the surfactant system comprises a surfactant selected from the group consisting of anionic surfactants, cationic surfactants, non-ionic surfactants, zwitterionic surfactants and/or amphoteric surfactants. In at least one embodiment, the surfactant is selected from the group consisting of anionic surfactants, cationic surfactants, non-ionic surfactants, zwitterionic surfactants and/or amphoteric surfactants.

In at least one embodiment, the composition comprises a total amount of surfactant of from 0.01 wt.-% to 70 wt.-%, from 0.1 wt.-% to 40%, from 1 wt.-% to 30%, from 2 wt.-% to 20 wt.-%.

In at least one embodiment, the composition comprises an anionic surfactant. In at least one embodiment, the composition comprises an anionic surfactant as cosmetically acceptable component (II). In at least one embodiment, the anionic surfactant is selected from the group consisting of (C$_{10}$-C$_{20}$)-alkyl and alkylene carboxylates, alkyl ether carboxylates, fatty alcohol sulfates, fatty alcohol ether sulfates, alkylamide sulfates and sulfonates, fatty acid alkylamide polyglycol ether sulfates, alkanesulfonates and hydroxyalkanesulfonates, olefinsulfonates, acyl esters of isethionates, α-sulfo fatty acid esters, alkylbenzenesulfonates, alkyl-phenol glycol ether sulfonates, sulfosuccinates, sulfosuccinic monoesters and diesters, fatty alcohol ether phosphates, protein/fatty acid condensation products, alkyl monoglyceride sulfates and sulfonates, alkylglyceride ether sulfonates, fatty acid methyltaurides, fatty acid sarcosinates, sulforicinoleates, acylglutamates, and mixtures thereof. The anionic surfactants (and their mixtures) can be used in the form of their water-soluble or water-dispersible salts, examples being the sodium, potassium, magnesium, ammonium, mono-, di-, and triethanolammonium, and analogous alkylammonium salts. In at least one embodiment, the anionic surfactant is the salt of an anionic surfactant comprising 12 to 14 carbon atoms. In at least one embodiment, the anionic surfactant is selected from the group consisting of sodium lauryl sulfate, sodium laureth sulfate, sodium tridecyl sulfate, sodium trideceth sulfate, sodium myristyl sulfate, sodium myreth sulfate, and mixtures thereof. Typical anionic surfactants for use in compositions of the invention include sodium oleyl succinate, ammonium lauryl sulphosuccinate, sodium lauryl sulphate, sodium lauryl ether sulphate, sodium lauryl ether sulphosuccinate, ammonium lauryl sulphate, ammonium lauryl ether sulphate, sodium dodecyl benzene sulphonate, triethanolamine dodecylbenzene sulphonate, sodium cocoyl isethionate, sodium lauryl isethionate, lauryl ether carboxylic acid and sodium N-lauryl sarcosinate. Preferred anionic surfactants are selected from sodium lauryl sulphate and sodium lauryl ether sulphate(n) EO, (where n is from 1 to 3); more preferably sodium lauryl ether sulphate(n)EO, (where n is from 1 to 3); most preferably sodium lauryl ether sulphate(n)EO where n=1. Preferably the level of alkyl ether sulphate is from 0.5 wt.-% to 25 wt.-% of the total composition, more preferably from 3 wt.-% to 18 wt.-%, most preferably from 6 wt.-% to 15 wt.-% of the total composition.

The total amount of anionic surfactant in the composition may range from 0.5 wt.-% to 45 wt.-%, more preferably from 1.5 wt.-% to 20 wt.-%.

In at least one embodiment, the composition comprises a fatty acyl isethionate. In at least one embodiment, the composition comprises fatty acyl isethionate at a level of from 1 to 10 wt.-%, more preferably from 2 to 8 wt.-%, most preferably from 2.5 to 7.5 wt.-%. A preferred fatty acyl isethionate product comprises fatty acyl isethionate surfactant at a level of from 40 to 80 wt.-% of the product, as well as free fatty acid and/or fatty acid salt at a level of from 15 to 50 wt. %. Preferably, greater than 20 wt.-% and less than 45 wt.-%, more preferably greater than 25 wt.-% and less than 45 wt.-% of the fatty acyl isethionate are of chain length greater than or equal to C6; and greater than 50 wt.-%, preferably greater than 60 wt.-% of the free fatty acid/soap is of chain length C$_6$ to C$_{20}$. In addition, the composition may contain isethionates salts which are present typically at levels less than 5 wt.-%, and traces (less than 2 wt.-%) of other impurities. Preferably, a mixture of aliphatic fatty acids is used for the preparation of commercial fatty acyl isethionates surfactants. The resulting fatty acyl isethionate surfactants (e.g., resulting from reaction of alkali metal isethionate and aliphatic fatty acid) preferably should have more than 20 wt.-%, preferably more than 25 wt.-%, but no more than 45 wt.-%, preferably 35% (on basis of fatty acyl isethionates reaction product) of fatty acyl group with 16 or greater carbon atoms to provide both excellent lather and mildness of the resulting fatty acyl isethionate product. These longer chain fatty acyl isethionate surfactants and fatty acids, i.e. fatty acyl group and fatty acid with 16 or more carbons, can typically form insoluble surfactant/fatty acid crystals in water at ambient temperatures.

In at least one embodiment, the composition comprises an acylglycinate surfactant. In at least one embodiment, the acylglycinate surfactant conforms to the formula (Y):

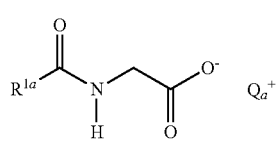

(Y)

wherein $R^{1a}$ is a linear or branched, saturated alkanoyl group having 6 to 30, preferably 8 to 22, particularly preferably 8 to 18, carbon atoms or is a linear or branched, mono- or polyunsaturated alkenoyl group having 6 to 30, preferably 8 to 22 and particularly preferably 12 to 18 carbon atoms, and $Q_a^+$ is a cation. In at least one embodiment, $Q_a^+$ is selected from the group consisting of $Li^+$, $Na^+$, $K^+$, $Mg^{++}$, $Ca^{++}$, $Al^{+++}$, $NH_4^+$, a monoalkylammmonium ion, a dialkylammonium ion, a trialkylammonium ion and a tetraalkylammonium ion, or combinations thereof.

Optionally $R^{1a}$ is independently from one another, are $(C_1-C_{22})$-alkyl radicals or $(C_2-C_{10})$-hydroxyalkyl radicals. In at least one embodiment, the acylglycinate surfactant is selected from sodium cocoylglycinate and potassium cocoylglycinate. In at least one embodiment, the acylglycinate surfactant is selected from those conforming to formula (Y), wherein R is $C_{12}$ alkyl or $C_{14}$ alkyl. In at least one embodiment, the acylglycinate surfactant is selected from those conforming to formula (Y), wherein R is $C_{16}$ alkyl or $C_{18}$ alkyl.

In at least one embodiment, the composition comprises from 0.01 wt.-% to 30 wt.-%, or 1 wt.-% to 25 wt.-%, preferably from 5 wt.-% to 20 wt.-%, more preferably from 12 wt.-% to 18 wt.-% acylglycinate surfactant.

In at least one embodiment, the composition comprises a glutamate surfactant corresponding to formula (Z) or a salt thereof:

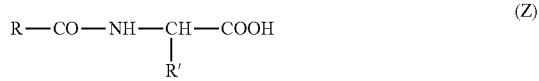

(Z)

wherein

R' is $HOOC-CH_2-CH_2-$ or $M^{+-}OOC-CH_2-CH_2-$ wherein $M^+$ is a cation; and wherein R is a linear or branched, saturated alkanoyl group having 6 to 30, preferably 8 to 22, more preferably 8 to 18, carbon atoms or is a linear or branched, mono- or polyunsaturated alkenoyl group having 6 to 30, preferably 8 to 22 and more preferably 12 to 18 carbon atoms. In at least one embodiment, $M^+$ is a metal cation. In at least one embodiment, $M^+$ is selected from the group consisting of $Li^+$, $Na^+$, $K^+$, $Mg^{++}$, $Ca^{++}$, $Al^{+++}$, $NH_4^+$, a monoalkylammmonium ion, a dialkylammonium ion, a trialkylammonium ion and a tetraalkylammonium ion, or combinations thereof. In at least one embodiment, the glutamate surfactant is selected from sodium cocoyl glutamate and potassium cocoyl glutamate. In at least one embodiment, the glutamate surfactant is selected from those conforming to formula (Z), wherein R is $C_{12}$ alkyl or $C_{14}$ alkyl. In at least one embodiment, the glutamate surfactant is selected from those conforming to formula (Z), wherein R is $C_{16}$ alkyl or $C_{18}$ alkyl. In at least one embodiment, the composition comprises from 0.01 wt.-% to 30 wt.-%, or 1 wt.-% to 25 wt.-%, preferably from 5 wt.-% to 20 wt.-%, more preferably from 12 wt.-% to 18 wt.-% glutamate surfactant.

In at least one embodiment, the composition comprises a non-ionic surfactant. The non-ionic surfactants may be present in the range 0 to 5 wt.-%. The non-ionic surfactants that can be included in the compositions herein include condensation products of aliphatic primary or secondary linear or branched chain alcohols or phenols with alkylene oxides, usually ethylene oxide and generally having from 6 to 30 ethylene oxide groups. Alkyl ethoxylates are particularly preferred. Most preferred are alky ethoxylates having the formula $$R-(OCH_2CH_2)_n OH$$

where

R is an alkyl chain of $C_{12}$ to $C_{15}$, and n is 5 to 9.

Other suitable nonionic surfactants include mono- or di-alkyl alkanolamides. Examples include coco mono- or di-ethanolamide and coco mono-isopropanolamide.

Further nonionic surfactants which can be included in compositions of the invention are the alkyl polyglycosides (APGs). Typically, APG is one which comprises an alkyl group connected (optionally via abridging group) to a block of one or more glycosyl groups. Preferred APGs are defined by the following formula:

$$RO-(G)n$$

wherein

R is a branched or straight chain alkyl group which may be saturated or unsaturated and G is a saccharide group.

R may represent a mean alkyl chain length of from about $C_5$ to about $C_{20}$.

Preferably R represents a mean alkyl chain length of from about $C_9$ to about $C_{12}$. G may be selected from $C_5$ or $C_6$ monosaccharide residues, and is preferably a glucoside. G may be selected from the group comprising glucose, xylose, lactose, fructose, mannose and derivatives thereof. Preferably G is glucose. The degree of polymerisation, n, may have a value of from about 1 to about 10 or more. Most preferably the value of n lies from about 1.3 to about 1.5. Suitable alkyl polyglycosides for use in the invention are commercially available and include for example those materials identified as: Oramix NS10 ex Seppic; Plantaren 1200 and Plantaren 2000 ex Henkel.

In at least one embodiment, the non-ionic surfactant has an HLB (Hydrophilic Lipophilic Balance) of greater than 12. Optionally, the non-ionic surfactant is selected from the group consisting of ethoxylated or ethoxylated/propoxylated fatty alcohols with a fatty chain comprising from 12 to 22 carbon atoms, ethoxylated sterols, such as stearyl- or lauryl alcohol (EO-7), PEG-16 soya sterol or PEG-10 soya sterol, polyoxyethylene polyoxypropylene block polymers (poloxamers), and mixtures thereof.

In at least one embodiment, the non-ionic surfactant is selected from the group consisting of ethoxylated fatty alcohols, fatty acids, fatty acid glycerides or alkylphenols, in particular addition products of from 2 to 30 mol of ethylene oxide and/or 1 to 5 mol of propylene oxide onto $C_8$- to $C_{22}$-fatty alcohols, onto $C_{12}$- to $C_{22}$-fatty acids or onto alkyl phenols having 8 to 15 carbon atoms in the alkyl group, $C_{12}$- to $C_{22}$-fatty acid mono- and diesters of addition products of from 1 to 30 mol of ethylene oxide onto glycerol, addition products of from 5 to 60 mol of ethylene oxide onto castor oil or onto hydrogenated castor oil, fatty acid sugar esters, in particular esters of sucrose and one or two $C_8$- to $C_{22}$-fatty acids, INCI: Sucrose Cocoate, Sucrose Dilaurate, Sucrose Distearate, Sucrose Laurate, Sucrose Myristate, Sucrose Oleate, Sucrose Palmitate, Sucrose Ricinoleate, Sucrose Stearate, esters of sorbitan and one, two or three $C_8$- to $C_{22}$-fatty acids and a degree of ethoxylation of from 4 to 20, polyglyceryl fatty acid esters, in particular of one, two or more $C_8$- to $C_{22}$-fatty acids and polyglycerol having preferably 2 to 20 glyceryl units, alkyl glucosides, alkyl oligoglucosides and alkyl polyglucosides having $C_8$ to $C_{22}$-alkyl groups, e.g. decylglucoside or laurylglucoside, and mixtures thereof.

In at least one embodiment, the non-ionic surfactant is selected from the group consisting of fatty alcohol ethoxylates (alkylpolyethylene glycols), alkylphenol polyethylene glycols, alkylmercaptan polyethylene glycols, fatty amine ethoxylates (alkylaminopolyethylene glycols), fatty acid ethoxylates (acylpolyethylene glycols), polypropylene glycol ethoxylates (Pluronics®), fatty acid alkylol amides, (fatty acid amide polyethylene glycols), N-alkyl-, N-alkoxypolyhydroxy-fatty acid amide, sucrose esters, sorbitol esters, polyglycol ethers, and mixtures thereof.

Other sugar-derived nonionic surfactants which can be included in compositions of the invention include the fatty (e.g. $C_{10}$-$C_{18}$)N-alkyl ($C_1$-$C_6$) polyhydroxy fatty acid amides, such as the $C_{12}$-$C_{18}$ N-methyl glucamides, as described for example in WO9206154A1 (Mao, P&G), and the N-alkoxy polyhydroxy fatty acid amides. In at least one embodiment, the composition comprises a fatty N-methyl-N-glucamide surfactant. In at least one embodiment, the fatty N-methyl-N-glucamide surfactant conforms to the formula (X):

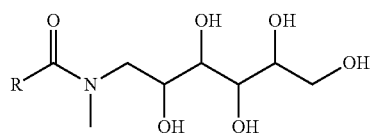

wherein
R is a linear or branched alkyl or alkenyl group having from 3 to 30 carbon atoms.

In at least one embodiment, R is an alkyl group having from 3 to 30 carbon atoms. In at least one embodiment, R is a saturated aliphatic hydrocarbon group which can be linear or branched and can have from 3 to 20 carbon atoms in the hydrocarbon chain, preferably linear or branched. Branched means that a lower alkyl group such as methyl, ethyl or propyl is present as substituent on a linear alkyl chain. In at least one embodiment, R is selected from the group consisting of 1-propyl, 2-propyl, 1-butyl, 2-butyl, 2-methyl-1-propyl (isobutyl), 2-methyl-2-propyl (tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, 1-heptyl, 1-octyl, 1-nonyl, 1-decyl, 1-undecyl, 1-dodecyl, 1-tetradecyl, 1-hexadecyl and 1-octadecyl. Suitable fatty N-methyl-N-glucamide surfactants are described in Klug et al. WO2013178700A2 (Clariant) and Connor et al. EP0550637B1 (P&G), which are incorporated herein by reference. In at least one embodiment, the fatty N-methyl-N-glucamide surfactant is selected from those conforming to formula (X), wherein R is $C_{12}$ alkyl or $C_{14}$ alkyl. In at least one embodiment, the fatty N-methyl-N-glucamide surfactant is selected from those conforming to formula (X), wherein R is $C_{16}$ alkyl or $C_{18}$ alkyl.

In at least one embodiment, the composition comprises from 1 wt.-% to 20 wt.-%, more preferably from 2 wt.-% to 10 wt.-%, even more preferably from 3 wt.-% to 7 wt.-% non-ionic surfactant.

In at least one embodiment, the composition comprises from 1 wt.-% to 20 wt.-%, more preferably from 2 wt.-% to 10 wt.-%, even more preferably from 3 wt.-% to 7 wt.-% fatty N-methyl-N-glucamide surfactant.

Amphoteric or zwitterionic surfactant(s) can be included in the composition in an amount ranging from 0.5 wt.-% to about 8 wt.-%, preferably from 1 wt.-% to 4 wt.-% of the total composition.

In at least one embodiment, the amphoteric surfactants are selected from the group consisting of N—($C_{12}$-$C_{18}$)-alkyl-β-aminopropionates and N—($C_{12}$-$C_{18}$)-alkyl-β-iminodipropionates as alkali metal salts and mono-, di-, and trialkylammonium salts; N-acylaminoalkyl-N,N-dimethylacetobetaine, preferably N—($C_8$-$C_{18}$)-acylaminopropyl-N,N-dimethylacetobetaine, ($C_{12}$-$C_{18}$)-alkyl-dimethyl-sulfopropylbetaine, amphosurfactants based on imidazoline (trade name: Miranol®, Steinapon®), preferably the sodium salt of 1-(β-carboxymethyloxyethyl)-1-(carboxymethyl)-2-laurylimidazolinium; amine oxide, e.g., ($C_{12}$-$C_{18}$)-alkyl-dimethyl-amine oxide, fatty acid amidoalkyldimethylamine oxide, and mixtures thereof.

In at least one embodiment, the composition comprises a betaine surfactant. Optionally, the betaine surfactant is selected from $C_8$- to $C_{18}$-alkylbetaines. In at least one embodiment, the betaine surfactant is selected from the group consisting of cocodimethylcarboxymethylbetaine, lauryldimethylcarboxymethylbetaine, lauryldimethylalphacarboxyethylbetaine, cetyldimethylcarboxymethylbetaine, oleyldimethylgammacarboxypropylbetaine and laurylbis(2-hydroxypropyl)alphacarboxyethylbetaine and combinations thereof. Optionally, the betaine surfactant is selected from $C_8$- to $C_{18}$-sulfobetaines. In at least one embodiment, the betaine surfactant is selected from the group consisting of cocodimethylsulfopropylbetaine, stearyldimethylsulfopropylbetaine, lauryldimethyl-sulfoethylbetaine, laurylbis(2-hydroxyethyl)sulfopropylbetaine, and combinations thereof. Optionally, the betaine surfactant is selected from carboxyl derivatives of imidazole, the $C_8$- to $C_{18}$-alkyldimethylammonium acetates, the $C_8$- to $C_{18}$-alkyldimethylcarbonylmethylammonium salts, and the $C_8$- to $C_{18}$-fatty acid alkylamidobetaines, and mixtures thereof.

Optionally, the $C_8$- to $C_{18}$-fatty acid alkylamidobetaine is selected from coconut fatty acid amidopropylbetaine, N-coconut fatty acid amidoethyl-N-[2-(carboxymethoxy)ethyl] glycerol (CTFA name: Cocoamphocarboxyglycinate), and mixtures thereof. A particularly preferred amphoteric or zwitterionic surfactant is cocamidopropyl betaine. Mixtures of any of the foregoing amphoteric or zwitterionic surfactants may also be suitable. Preferred mixtures are those of cocamidopropyl betaine with further amphoteric or zwitterionic surfactants as described above. A preferred further amphoteric or zwitterionic surfactant is sodium cocoamphoacetate.

In at least one embodiment, the composition comprises from 0.5 wt.-% to 20 wt.-%, preferably from 1 wt.-% to 10 wt.-% amphoteric surfactant.

In at least one embodiment, the composition comprises a surfactant system. In at least one embodiment, the surfactant system comprises at least one surfactant selected from the group consisting of lauryl sulfate, laureth sulfate, cocoamido-propylbetaine, sodium cocoylglutamate, lauroamphoacetate, and mixtures thereof. In at least one embodiment, the surfactant system comprises sodium laureth sulphate, sodium lauryl sulphate, and optionally cocamidopropyl betaine. In at least one embodiment, the surfactant system comprises sodium laureth sulphate, Potassium Cocyl Glutamate, and cocamidopropyl betaine.

Auxiliary

In at least one embodiment, the composition comprises at least one additive common in cosmetology, pharmacy, and dermatology, which are hereinafter called auxiliaries. In at least one embodiment, the composition comprises an auxiliary. In at least one embodiment, the auxiliary is cosmetically acceptable. In at least one embodiment, the auxiliary is selected from the group consisting of oily substances, waxes, emulsifiers, coemulsifiers, solubilizers, cationic polymers, film formers, superfatting agents, refatting agents, foam stabilizers, stabilizers, active biogenic substances, preservatives, preservation boosting ingredients, anti-fungal substances, anti-dandruff agents, dyes or pigments, particulate substances, opacifiers, abrasives, absorbents, anticaking agents, bulking agents, pearlizing agents, direct dyes, perfumes or fragrances, carriers, solvents or diluents, propellants, functional acids, active ingredients, skin-brightening agents, self-tanning agents, exfoliants, enzymes, anti-acne agents, deodorants and anti-perspirants, viscosity modifiers, thickening and gelling agents, pH adjusting agents, buffering agents, anti-oxidants, chelants, astringents, sunscreens, sun protection agents, UV filters, skin conditioning agents, emollients, humectants, occlusive agents, pediculocides, anti-foaming agents, flavouring agents, electrolytes, oxidizing agents and reducing agents.

In at least one embodiment, the composition comprises an oily substance or wax. In at least one embodiment, the composition comprises an oily substance or wax, wherein the oily substance or wax are selected from the group consisting of silicone oils, volatile or nonvolatile, linear, branched or cyclic, optionally with organic modification; phenylsilicones; silicone resins and silicone gums; mineral oils such as paraffin oil or vaseline oil; oils of animal origin such as perhydrosqualene, lanolin; oils of plant origin such as liquid triglycerides, e.g., sunflower oil, corn oil, soybean oil, rice oil, jojoba oil, babassu oil, pumpkin oil, grapeseed oil, sesame oil, walnut oil, apricot oil, macadamia oil, avocado oil, sweet almond oil, lady's-smock oil, castor oil, triglycerides of caprylic/capric acids, olive oil, peanut oil, rapeseed oil, argan oil, abyssinian oil, and coconut oil; synthetic oils such as purcellin oil, isoparaffins, linear and/or branched fatty alcohols and fatty acid esters, preferably guerbet alcohols having 6 to 18, preferably 8 to 10, carbon atoms; esters of linear ($C_6$-$C_{13}$) fatty acids with linear ($C_6$-$C_{20}$) fatty alcohols; esters of branched ($C_6$-$C_{13}$) carboxylic acids with linear ($C_6$-$C_{20}$) fatty alcohols, esters of linear ($C_6$-$C_{18}$) fatty acids with branched alcohols, especially 2-ethylhexanol; esters of linear and/or branched fatty acids with polyhydric alcohols (such as dimerdiol or trimerdiol, for example) and/or guerbet alcohols; triglycerides based on ($C_6$-$C_{10}$) fatty acids; esters such as dioctyl adipate, diisopropyl dimer dilinoleate; propylene glycols/dicaprylate or waxes such as beeswax, paraffin wax or microwaxes, alone or in combination with hydrophilic waxes, such as cetylstearyl alcohol, for example; fluorinated and perfluorinated oils; fluorinated silicone oils; mixtures of the aforementioned compounds.

In at least one embodiment, the composition comprises an oily substance, which is any fatty substance which is liquid at room temperature (25° C.). In a preferred embodiment, the oily substance is selected from the group consisting of sweet almond oil, caprylic/capric triglycerides, dimethicone, mineral oil, squalane, castor oil, isopropyl isostearate, jojoba oil, dicaprylyl carbonate, isohexadecane, $C_{12}$-$C_{15}$ alkyl benzoate, and combinations thereof. In at least one embodiment, the composition comprises from 0.001 wt.-% to 60 wt.-%, preferably from 0.05 wt.-% to 50 wt.-%, even more preferably from 0.1 wt.-% to 40 wt.-% of at least one oily substance.

In a preferred embodiment, the wax is selected from the group consisting of carnauba wax, beeswax, candelilla wax, synthetic wax, polyethylene, paraffin wax, microcrystalline wax, hydrogenated vegetable oil, hydrogenated castor oil, rice bran wax, cetyl dimethicone, bis-PEG-18 methyl ether dimethyl silane, and combinations thereof. In at least one embodiment, the composition comprises from 0.001 wt.-% to 30 wt.-%, preferably from 0.05 wt.-% to 20 wt.-%, even more preferably from 0.1 wt.-% to 10 wt.-% of at least one wax.

In at least one embodiment, the composition comprises an emulsifier, coemulsifier or solubilizer. Non-ionic, anionic, cationic or amphoteric surface active compounds can be used as emulsifiers, coemulsifiers and solubilizers.

As nonionogenic surface active compounds, consideration may preferably be given to: addition products of 0 to 30 mol ethylene oxide and/or 0 to 5 mol propylene oxide on linear fatty alcohols with 8 to 22 carbon atoms, on fatty acids with 12 to 22 carbon atoms, on alkyl phenols with 8 to 15 carbon atoms in the alkyl group and on sorbitan or sorbitol esters; ($C_{12}$-$C_{18}$)-fatty acid mono- and diesters of addition products of 0 to 30 mol ethylene oxide on glycerol; glycerol mono- and diesters and sorbitan mono- and diesters of saturated and unsaturated fatty acids with 6 to 22 carbon atoms and optionally their ethylene oxide addition products; addition products of 15 to 60 mol ethylene oxide on castor oil and/or hardened castor oil; polyol and especially polyglycerol esters, e.g. polyglycerol polyricinoleate and polyglycerol poly-12-hydroxystearate. Ethoxylated fatty amines, fatty acid amides, fatty acid alkanolamides and mixtures of compounds from several of these classes of substances are also preferably suitable. Polymeric ethers formed by block polymerization of ethylene or propylene oxide known as poloxamers are also suitable.

Suitable ionogenic coemulsifiers are e.g. anionic emulsifiers, such as mono-, di- or triphosphoric acid esters, soaps (e.g. sodium stearate), fatty alcohol sulfates as well as cationic emulsifiers such as mono-, di- and tri-alkyl quats and polymeric derivatives thereof.

Amphoteric emulsifiers that are available are preferably alkyl aminoalkyl carboxylic acids, betaines, sulfobetaines and imidazoline derivatives.

Fatty alcohol ethoxylates are used especially preferably, and may be selected from the group consisting of ethoxylated stearyl alcohols, isostearyl alcohols, cetyl alcohols, isocetyl alcohols, oleyl alcohols, lauryl alcohols, isolauryl alcohols and cetylstearyl alcohols, especially polyethylene glycol (13) stearyl ether, polyethylene glycol (14) stearyl ether, polyethylene glycol (15) stearyl ether, polyethylene glycol (16) stearyl ether, polyethylene glycol (17) stearyl ether, polyethylene glycol (18) stearyl ether, polyethylene glycol (19) stearyl ether, polyethylene glycol (20) stearyl ether, polyethylene glycol (12) isostearyl ether, polyethylene glycol (13) isostearyl ether, polyethylene glycol (14) isostearyl ether, polyethylene glycol (15) isostearyl ether, polyethylene glycol (16) isostearyl ether, polyethylene glycol (17) isostearyl ether, polyethylene glycol (18) isostearyl ether, polyethylene glycol (19) isostearyl ether, polyethylene glycol (20) isostearyl ether, polyethylene glycol (13) cetyl ether, polyethylene glycol (14) cetyl ether, polyethylene glycol (15) cetyl ether, polyethylene glycol (16) cetyl ether, polyethylene glycol (17) cetyl ether, polyethylene glycol (18) cetyl ether, polyethylene glycol (19) cetyl ether, polyethylene glycol (20) cetyl ether, polyethylene glycol (13) isocetyl ether, polyethylene glycol (14) isocetyl ether, polyethylene glycol (15) isocetyl ether, polyethylene glycol (16) isocetyl ether, polyethylene glycol (17) isocetyl ether, polyethylene glycol (18) isocetyl ether, polyethylene glycol (19) isocetyl ether, polyethylene glycol (20) isocetyl ether, polyethylene glycol (12) oleyl ether, polyethylene glycol (13) oleyl ether, polyethylene glycol (14) oleyl ether, polyethylene glycol (15) oleyl ether, polyethylene glycol (12) lauryl ether, polyethylene glycol (12) isolauryl ether, polyethylene glycol (13) cetylstearyl ether, polyethylene glycol (14) cetylstearyl ether, polyethylene glycol (15) cetylstearyl ether, polyethylene glycol (16) cetylstearyl ether, polyethylene glycol (17) cetylstearyl ether, polyethylene glycol (18) cetylstearyl ether, polyethylene glycol (19) cetylstearyl ether.

Fatty acid ethoxylates are also preferred, and may be selected from the group consisting of ethoxylated stearates, isostearates and oleates, especially polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

Sodium laureth-11-carboxylate can be used advantageously as ethoxylated alkyl ether carboxylic acid or salts thereof.

Polyethylene glycol (60) evening primrose glycerides can be used advantageously as ethoxylated triglycerides.

Furthermore, it is advantageous to select the polyethylene glycol glycerol fatty acid ester from the group polyethylene glycol (20) glyceryl laurate, polyethylene glycol (6) glyceryl caprate/caprinate, polyethylene glycol (20) glyceryl oleate, polyethylene glycol (20) glyceryl isostearate and polyethylene glycol (18) glyceryl oleate/cocoate.

Among the sorbitan esters, the following are especially suitable: polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

Especially advantageous coemulsifiers are glyceryl monostearate, glyceryl monooleate, diglyceryl monostearate, glyceryl isostearate, polyglyceryl-3-oleate, polyglyceryl-3-diisostearate, polyglyceryl-4-isostearate, polyglyceryl-2-dipolyhydroxystearate, polyglyceryl-4-dipolyhydroxystearate, PEG-30-dipolyhydroxystearate, diisostearoylpolyglyceryl-3-diisostearate, glycol distearate and polyglyceryl-3-dipolyhydroxystearate, sorbitan monoisostearate, sorbitan stearate, sorbitan oleate, sucrose distearate, lecithin, PEG-7-hydrogenated castor oil, cetyl alcohol, stearyl alcohol, behenyl alcohol, isobehenyl alcohol and polyethylene glycol (2) stearyl ether (steareth-2), alkyl methicone copolyols and alkyl dimethicone copolyols, especially cetyldimethicone copolyol (ABIL® EM 90) or laurylmethicone copolyol.

In a preferred embodiment, the emulsifier, coemulsifier or solubilizer is selected from the group consisting of glyceryl stearate, cetearyl alcohol, polysorbate 20, stearic acid, cetearyl glucoside, PEG-40 hydrogenated castor oil, cetyl phosphate, steareth-2, ceteth-10 phosphate, trilaureth-4 phosphate, polyglyceryl-2 sesquiisostearate, cetyl PEG/PPG-10/1 dimethicone, cetrimonium chloride, and combinations thereof.

In at least one embodiment, the composition comprises from 0.1 wt.-% to 20 wt.-%, preferably from 0.5 wt.-% to 10 wt.-%, even more preferably from 1.0 wt.-% to 5.0 wt.-% of at least one emulsifier, coemulsifier and/or solubilizer.

In at least one embodiment, the composition comprises a cationic polymer. Suitable cationic polymers include those known under the INCI designation "polyquaternium", especially polyquaternium-31, polyquaternium-16, polyquaternium-24, Polyquaternium-7, polyquaternium-22, polyquaternium-39, polyquaternium-28, polyquaternium-2, polyquaternium-10, polyquaternium-11, and also polyquaternium-37 & mineral oil & PPG trideceth (Salcare SC95), PVP-dimethylaminoethyl methacrylate copolymer, guar-hydroxypropyltriammonium chlorides, and also calcium alginate and ammonium alginate. It is additionally possible to employ cationic cellulose derivatives; cationic starch; copolymers of diallylammonium salts and acrylamides; quaternized vinylpyrrolidone/vinylimidazole polymers; condensation products of polyglycols and amines; quaternized collagen polypeptides; quaternized wheat polypeptides; polyethyleneimines; cationic silicone polymers, such as amidomethicones, for example; copolymers of adipic acid and dimethylaminohydroxypropyldiethylenetriamine; polyaminopolyamide and cationic chitin derivatives, such as chitosan, for example.

In a preferred embodiment, the cationic polymer is selected from the group consisting of polyquaternium-10, guar hydroxypropyltrimonium chloride, polyquaternium-7, polyquaternium-6, and combinations thereof.

In at least one embodiment, the composition comprises from 0.1 wt.-% to 10 wt.-%, preferably from 0.5 wt.-% to 7.5 wt.-%, even more preferably from 1.0 wt.-% to 5.0 wt.-% of at least one cationic polymer.

In at least one embodiment, the composition comprises a film former. Film formers are materials which produce a continuous film on skin, hair, or nails such as synthetic or natural polymers and their derivatives. The compositions according to the invention can contain film formers, which are, depending on the intended use, selected from salts of phenylbenzimidazole sulfonic acid, water-soluble polyurethanes, for example C10-polycarbamyl polyglyceryl ester, polyvinyl alcohol, polyvinylpyrrolidone (PVP) copolymers, vinylpyrrolidone/vinyl acetate copolymer or PVP/eicosene copolymers, vinylpyrrolidone/alkene copolymers, for example VP/eicosene copolymer or VP/hexadecene copolymer, PVM/MA copolymer or esters thereof, maleinized polypropylene polymers, water-soluble acrylic acid polymers/copolymers or esters or salts thereof, for example partial-ester copolymers of acrylic/methacrylic acid, polyalkylsilsesquioxanes, polyacrylamide, water-soluble cellulose, for example hydroxymethylcellulose, hydroxyethylcellulose, hydroxypropylcellulose, water-soluble quaterniums, polyquaterniums, carboxyvinyl polymers, such as carbomers and salts thereof, polysaccharides, for example polydextrose and glucan, vinyl acetate/crotonate.

In a preferred embodiment, the film former is selected from the group consisting of VP/eicosene copolymer, PVP, VP/VA copolymer, styrene/acrylates copolymer, acrylates copolymer, butyl ester of PVM/MA copolymers, hydroxyethylcellulose, polyquaternium-10, polypropylsilsesquioxane, polyurethane-64, and combinations thereof.

In at least one embodiment, the composition comprises from 0.1 wt.-% to 10 wt.-%, preferably from 0.5 wt.-% to 7.5 wt.-%, even more preferably from 1.0 wt.-% to 5.0 wt.-% of at least one film former.

In at least one embodiment, the composition comprises a superfatting agent and/or a refatting agent. As superfatting agents it is possible to use substances such as, for example, lanolin, polyethoxylated lanolin derivatives, lecithin, lecithin derivatives, non-ethoxylated and polyethoxylated or acylated lanolin and lecithin derivatives, polyol fatty acid esters such as glyceryl oleate, mono-, di- and triglycerides and/or fatty acid alkanolamides, can preferably be used as overfatting agents or refatting agents. These compounds can also simultaneously serve as foam stabilizers. In a preferred embodiment, the superfatting agent and/or a refatting agent is selected from the group consisting of, lanolin, glyceryl ricinoleate, PEG-8 glyceryl laurate, glyceryl oleate, cocamide MEA, PEG-75 lanolin, and combinations thereof. In at least one embodiment, the composition comprises from 0.01 wt.-% to 10 wt.-%, preferably from 0.1 wt.-% to 5.0 wt.-%, even more preferably from 0.5 wt.-% to 3.0 wt.-% of at least one superfatting agent and/or a refatting agent.

In at least one embodiment, the composition comprises a stabiliser. As stabiliser it is possible to use metal salts of fatty acids, such as magnesium, aluminum and/or zinc stearate, for example. In a preferred embodiment, the stabilizer is selected from the group consisting of, aluminum stearate, aluminum isostearates/myristates, magnesium stearate, magnesium cocoate, zinc palmitate, zinc stearate, and combinations thereof. In at least one embodiment, the composition comprises from 0.01 wt.-% to 10 wt.-%, preferably from 0.5 wt.-% to 8.0 wt.-%, even more preferably from 1.0 wt.-% to 5.0 wt.-% of at least one stabilizer.

In at least one embodiment, the composition comprises a biogenic substance. In at least one embodiment, the composition comprises a biogenic substance, wherein such substances are selected from plant extracts (e.g. leaf, root, seed, flower and/or stem extracts from aloe vera, camomile, green tea, hamamelis or licorice), local anesthetics, antibiotics, antiphlogistics, antiallergic agents, hormones, beta-glucans, cholesterol, amino acids, ceramides, corticosteroids, sebostatics, Bisabolol®, allantoin, Phytantriol®, proteins, vitamins selected from niacin, biotin, vitamin B2, vitamin B3, vitamin B6, vitamin B5, vitamin B3 derivatives (salts, acids, esters, amides, alcohols), vitamin C and vitamin C derivatives (salts, acids, esters, amides, alcohols), preferably as sodium salt of the monophosphoric acid ester of ascorbic acid or as magnesium salt of the phosphoric acid ester of ascorbic acid, tocopherol and tocopherol acetate, vitamin E and/or its derivatives, protein derivatives such as gelatin, collagen hydrolysates, polypeptides, egg yolk, lecithin, hydrolyzed silk, hydrolyzed keratin, milk protein, cerebrosides or phospholipids. In a preferred embodiment, the biogenic active substance is selected from the group consisting of, aloe vera extract, collagen hydrolysates, bisabolol, vitamin C, vitamin E, allantoin, vitamin B5, tocopherol acetate, retinyl palmitate, and combinations thereof. In at least one embodiment, the composition comprises from 0.001 wt.-% to 5.0 wt.-%, preferably from 0.01 wt.-% to 3.0 wt.-%, even more preferably from 0.1 wt.-% to 2.0 wt.-% of at least one biogenic active substance.

In at least one embodiment, the composition comprises a preservative, preservation boosting ingredient, anti-fungal agent, and/or anti-dandruff agent. In at least one embodiment, the preservative is selected from the group consisting of benzyl alcohol, Piroctone Olamine, phenoxyethanol, parabens, pentanediol, benzoic acid/sodium benzoate, sorbic acid/potassium sorbate, and combinations thereof. Other organic acids can also be used to provide antimicrobial protection. In at least one embodiment, the preservation boosting ingredient is selected from the group consisting of anisic acid, lactic acid, sorbitan caprylate, ethylhexylglycerin, caprylyl glycol, octanediol, and mixtures thereof. A suitable preservation boosting ingredient is also disclosed in International patent application WO2018002100A1 (PCT/EP2017/065927) by Clariant International Ltd (see in particular claim 1 therein), which is incorporated herein by reference. In at least one embodiment, the composition comprises 0.01 to 5.0 wt.-%, particularly preferably from 0.05 wt.-% to 1.0 wt.-% of at least one preservative. Suitable preservatives include the substances listed in the International Cosmetic Ingredient Dictionary and Handbook, $9^{th}$ Edition with the function "preservatives". In at least one embodiment, the preservative is selected from the group consisting of phenoxyethanol, benzyl paraben, butyl paraben, ethyl paraben, isobutyl paraben, isopropyl paraben, methyl paraben, propyl paraben, iodopropynyl butylcarbamate, methyldibromoglutaronitrile, DMDM hydantoin and combinations thereof. In at least one embodiment, the composition comprises a preservative selected from the group consisting of cetyltrimethyl ammonium chloride, cetylpyridinium chloride, benzethonium chloride, diisobutylethoxyethyldimethyl benzylammonium chloride, sodium N-lauryl sarcosinate, sodium-N-palmethyl sarcosinate, lauroyl sarcosine, N-myristoylglycine, potassium-N-laurylsarcosine, trimethylammonium chloride, sodium aluminium chlorohydroxylactate, triethylcitrate, tricetylmethylammonium chloride, 2,4,4'-trichloro-2'-hydroxydiphenylether (Triclosan), phenoxyethanol, 1,5-pentandiol, 1,6-hexandiol, 3,4,4'-trichlorocarbanilide (Triclocarban), diaminoalkylamide, L-lysine hexadecylamide, heavy metal citrate salts, salicylate, piroctose, zinc salts, pyrithione and its heavy metal salts, zinc pyrithione, zinc phenol sulfate, farnesol, ketoconazol, oxiconazol, bifonazole, butoconazole, cloconazole, clotrimazole, econazole, enilconazole, fenticonazole, isoconazole, miconazole, sulconazole, tioconazole, fluconazole, itraconazole, terconazole, naftifine, terbinafine, selenium disulfide, methylchloroisothiazolinone, methylisothiazolinone, methyldibromo glutaronitrile, silver chloride (AgCl), diazolidinyl urea, imidazolidinyl urea, dehydroacetic acid, undecylenic acid, chlorphenesin, propionic acid, salicylic acid, chloroxylenol, sodium salts of diethylhexylsulfosuccinate, sodiumbenzoate, phenoxyethanol, (RS)-1-(4-chlorophenoxy)-1-imidazol-1-yl-3,3-dimethylbutan-2-one (climbazole), benzyl alcohol, phenoxyisopropanol, parabens such as butyl-, ethyl-, methyl- and propylparaben and their salts, 2-Bromo-2-nitropropane-1,3-diol, polyaminopropyl biguanide, phenoxyisopropanol, iodopropynyl butylcarbamate, benzalkonium chloride, benzethonium chloride, pentandiol, 1,2-octanediol, ethylhexylglycerin, sorbic acid, benzoic acid, lactic acid, imidazolidinyl urea, diazolidinyl urea, dimethylol dimethyl hydantoin (DMDMH), chlorhexidine, sodium salts of hydroxymethyl glycinate, hydroxyethylglycine of sorbic acid, and combinations thereof. In at least one embodiment, the preservative is selected from the group consisting of phenoxyethanol, benzyl paraben, butyl paraben, ethyl paraben, isobutyl paraben, isopropyl paraben, methyl paraben, propyl paraben, iodopropynyl butylcarbamate, methyldibromoglutaronitrile, DMDM hydantoin and combinations thereof. In at least one embodiment, the composition is substantially free of parabens.

In at least one embodiment, the composition comprises from 0.1 wt.-% to 5.0 wt.-% antimicrobial agents. In at least one embodiment, the antimicrobial agent is chlorhexidine.

In at least one embodiment, the composition comprises an anti-fungal substance. In at least one embodiment, the anti-fungal substance is selected from the group consisting of ketoconazole, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine, terbinafine, zinc pyrithione, Piroctone Olamine (Octopirox®), (RS)-1-(4-chlorophenoxy)-1-imidazol-1-yl-3,3-dimethylbutan-2-one (climbazole), and combinations thereof. In at least one embodiment, the composition comprises a total amount of anti-fungal substance in the composition of from 0.1 wt.-% to 1.0 wt.-%. In at least one embodiment, the composition comprises pyridinethione anti-dandruff particulates, for example 1-hydroxy-2-pyridinethione salts, are highly preferred particulate anti-dandruff agents. The concentration of pyridinethione anti-dandruff particulate may ranges from 0.1% to 4.0%, by weight of the formulation, preferably from 0.1% to 3.0%, more preferably from 0.3% to 2.0%. Preferred pyridinethione salts include those formed from heavy metals such as zinc, tin, cadmium, magnesium, aluminum and zirconium, preferably zinc, more preferably the zinc salt of 1-hydroxy-2-pyridinethione (known as "zinc pyridinethione" or "ZPT"), more preferably 1-hydroxy-2-pyridinethione salts in platelet particle form. Salts formed from other cations, such as sodium, may also be suitable. Pyridinethione anti-dandruff agents are described, for example, in US patents U.S. Pat. Nos. 2,809,971; 3,236,733; 3,761,418; 4,345,080; 4,323,683; 4,379,753; and 4,470,982. It is contemplated that when ZPT is used as the anti-dandruff particulate in the compositions herein, that the growth or regrowth of hair may be stimulated or regulated, or both, or that hair loss may be reduced or inhibited, or that hair may appear thicker or fuller.

In at least one embodiment, the composition comprises a preservative system comprising a plurality of different compounds selected from the group consisting of preservatives, preservation boosting ingredients, anti-fungal agents and anti-dandruff agents.

In at least one embodiment, the composition comprises a dye or pigment. In at least one embodiment, the composition comprises at least one dye or pigment. Suitable dyes and pigments are disclosed in WO2013017262A1 in the table spanning pages 36 to 43. These may be colored pigments which impart color effects to the product mass or to hair or skin, or they may be luster effect pigments which impart luster effects to the product mass or to the hair or skin. The color or luster effects on the hair or skin are preferably temporary, i.e. they last until the next hair or skin wash and can be removed again by washing the hair or skin with customary shampoos, body or face cleansers, body washes etc. or by using a make-up remover, micellar water or cleansing wipes. In at least one embodiment, the composition comprises a total amount of from 0.01 wt.-% to 25 wt.-%, preferably from 0.1 wt.-% to 15 wt.-%, even more preferably from 0.5 wt.-% to 10 wt.-% of at least one pigment. In at least one embodiment, the particle size of the pigment is from 1 micron to 200 micron, preferably from 3 micron to 150 micron, more preferably 10 micron to 100 micron. The pigments are colorants which are virtually insoluble in the application medium, and may be inorganic or organic. Inorganic-organic mixed pigments are also possible. Preference is given to inorganic pigments. The advantage of inorganic pigments is their excellent resistance to light, weather and temperature. The inorganic pigments may be of natural origin. In at least one embodiment, the inorganic pigment is selected from the group consisting of chalk, ochre, umber, green earth, burnt sienna, graphite, and combinations thereof. The pigments may be white pigments, such as, for example, titanium dioxide or zinc oxide, black pigments, such as, for example, iron oxide black, colored pigments, such as, for example, ultramarine or iron oxide red, lustre pigments, metal effect pigments, pearlescent pigments, and fluorescent or phosphorescent pigments, where preferably at least one pigment is a colored, nonwhite pigment. In at least one embodiment, the pigment is selected from the group consisting of metal oxides, hydroxides and oxide hydrates, mixed phase pigments, sulfur-containing silicates, metal sulfides, complex metal cyanides, metal sulfates, chromates and molybdates, and the metals themselves (bronze, silver, gold pigments), and combinations thereof. In at least one embodiment, the pigment is selected from the group consisting of titanium dioxide (CI 77891), black iron oxide (CI 77499), yellow iron oxide (CI 77492), red and brown iron oxide (CI 77491), manganese violet (CI 77742), ultramarine (sodium aluminum sulfosilicates, CI 77007, Pigment Blue 29), chromium oxide hydrate (CI 77289), Prussian blue (ferric ferrocyanide, CI 77510), carmine (cochineal), and combinations thereof. In at least one embodiment, the pigment is selected from the group consisting of pearlescent and colored pigments which consist of either single crystals like mica, silica, bismuth oxychloride, boron nitride or titanium dioxide or which have a layer-substrate structure based on mica, aluminium, aluminium oxide, titanium dioxide, silicium dioxide, silicates (e.g. calcium aluminium borosilicate, calcium sodium borosilicate, magnesium aluminium silicate or sodium magnesium fluorosilicate) which are coated with a metal oxide (e.g. iron oxide, chromium oxide, tin oxide) or a metal oxychloride, such as titanium dioxide or bismuth oxychloride, or a metal hydroxide, such as aluminum hydroxide, and optionally further color-imparting substances, such as Prussian blue, ultramarine, carmine or other organic dyes and where the color can be determined by varying the layer thickness. Such pigments are sold, for example, under the trade names RonaFlair®, Colorona®, Xirona®, and Timiron® by Merck or under the trade name Flamenco®, Timica® and Cloisonne® by BASF, Germany. The pearlescent effect can be controlled both by means of the particle size and by means of the particle size distribution of the pigment population. Suitable particle size distributions are e.g. in the range 2-50 µm, 5-25 µm, 5-40 µm, 5-60 µm, 5-95 µm, 5-100 µm, 10-60 µm, 10-100 µm, 10-125 µm, 20-100 µm, 20-150 µm, and <15 µm. A wider particle size distribution e.g. of 20-150 µm, produces glittering effects, whereas a narrower particle size distribution of <15 µm gives a uniform silky appearance. In a preferred embodiment, the pigment is selected from the group consisting of titanium dioxide (CI 77891), black iron oxide (CI 77499), yellow iron oxide (CI 77492), red and brown iron oxide (CI 77491), mica, silica, bismuth oxychloride, and combinations thereof. In at least one embodiment, the pigment is selected from the group consisting of organic pigments such as sepia, gamboge, bone charcoal, Cassel brown, indigo, chlorophyll and other plant pigments. In at least one embodiment, the pigment is selected from the group consisting of synthetic organic pigments such as azo pigments, anthraquinoids, indigoids, dioxazine, quinacridone, phthalocyanine, isoindolinone, perylene and perinone, metal complex, alkali blue and diketopyrrolopyrrole pigments.

In at least one embodiment, the composition comprises a particulate substance. In at least one embodiment, the composition comprises at least one particulate substance. Suitable substances are, for example, substances which are solid at room temperature (25° C.) and are in the form of particles. Suitable substances are, for example, substances which serve as opacifiers, abrasives, absorbents, anti-caking agents, bulking agents or performance fillers. In at least one embodiment, the particulate substance is selected from the group consisting of silica, silicates (e.g. sepiolite, montmorillonite, bentonite, kaolin, hectorite), aluminates, clay earths, mica, talc, starch, perlite, charcoal, pulp powder, seed powder, insoluble salts, in particular insoluble inorganic metal salts, metal oxides (e.g. titanium dioxide), minerals and insoluble polymer particles, such as polyamide derivatives (e.g. nylon-12, nylon-6, polyamide-5), silicones (e.g. polymethylsilsesquioxane), polyesters (e.g. polyester-12), polyethylene and polymethyl methacrylates. The particles are present in the composition in undissolved, preferably stably dispersed form, and, following application to the keratin substrate and evaporation of the solvent, can deposit on the substrate in solid form. A stable dispersion can be achieved by providing the composition with a yield point which is large enough to prevent the solid particles from sinking. An adequate yield point can be established using suitable gel formers in a suitable amount. In at least one embodiment, the particulate substance is selected from the group consisting of silica (silica gel, silicon dioxide) and metal salts, in particular inorganic metal salts, where silica is particularly preferred. Metal salts are, for example, alkali metal or alkaline earth metal halides, such as sodium chloride or potassium chloride; alkali metal or alkaline earth metal sulfates, such as sodium sulfate or magnesium sulfate. In a preferred embodiment, the particulate substance is selected from the group consisting of, silica, mica, bentonite, kaolin, talc, polymethylsilsesquioxane, polyethylene, clay, and combinations thereof. In at least one embodiment, the composition comprises from 0.01 wt.-% to 20 wt.-%, preferably from 0.05 wt.-% to 15 wt.-%, even more preferably from 0.5 wt.-% to 10 wt.-% of at least one particulate substance.

In at least one embodiment, the composition comprises pearlizing agents. In at least one embodiment, the composition comprises at least one pearlizing agent. In at least one embodiment, the particulate substance is selected from the group consisting of, fatty acid monoalkanolamides, fatty acid dialkanolamides, monoesters or diesters of alkylene glycols, especially ethylene glycol and/or propylene glycol or oligomers thereof, with higher fatty acids, e.g. palmitic acid, stearic acid and behenic acid, monoesters or polyesters of glycerol with carboxylic acids, fatty acids and metal salts thereof, ketosulfones or mixtures of the aforementioned compounds. In a preferred embodiment, the pearlizing agent is selected from the group consisting of, ethylene glycol distearates and/or polyethylene glycol distearates with 3 glycol units on average, and combinations thereof. In at least one embodiment, the composition comprises from 0.1 wt.-% to 15 wt.-%, preferably from 0.5 wt.-% to 10 wt.-%, even more preferably from 1.0 wt.-% to 5.0 wt.-% of at least one pearlizing agent.

In at least one embodiment, the composition comprises a direct dye. In at least one embodiment, the composition comprises at least one direct dye. Preferred among the direct dyes are the following compounds, alone or in combination with one another: hydroxyethyl-2-nitro-p-toluidine, 2-hydroxyethylpicramic acid, 4-nitrophenylaminourea, tri(4-amino-3-methylphenyl)carbenium chloride (Basic Violet 2), 1,4-di-amino-9,10-anthracenedione (Disperse Violet 1), 1-(2-hydroxy-ethyl)amino-2-nitro-4-[di(2-hydroxyethyl) amino]benzene (HC Blue No. 2), 4-[ethyl-(2-hydroxyethyl) amino]-1-[(2-hydroxyethyl)amino]-2-nitrobenzene hydrochloride (HC Blue No. 12), 1-amino-4-[di(2-hydroxyethyl) amino]-2-nitrobenzene hydrochloride (HC Red No. 13), 4-amino-1-[(2-hydroxyethyl)amino]-2-nitrobenzene (HC Red No. 3), 4-amino-3-nitrophenol, 4-[(2-hydroxyethyl) amino]-3-nitrophenol, 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-chloro-6-ethylamino-4-nitrophenol, 2-amino-6-chloro-4-nitrophenol, 4-[(2-hydroxyethyl) amino]-3-nitro-1-trifluoromethylbenzene (HC Yellow No. 13), 8-amino-2-bromo-5-hydroxy-4-imino-6-{[3-(trimethylammonio)-phenyl]amino}-1(4H)-naphthalenone chloride (C.I. 56059; Basic Blue No. 99), 1-[(4-aminophenyl)azo]-7-(trimethylammonio)-2-naphthol chloride (C.I. 12250; Basic Brown No. 16), 1-[(4-amino-2-nitrophenyl)azo]-7-(trimethylammonio)-2-naphthol chloride (Basic Brown No. 17), 2-hydroxy-1-[(2-methoxyphenyl)azo]-7-(trimethylammonio)naphthalene chloride (C.I. 12245; Basic Red No. 76), 3-methyl-1-phenyl-4-{[3-(trimethylammonio)phenyl] azo}pyrazol-5-one chloride (C.I. 12719; Basic Yellow No. 57) and 2,6-diamino-3-[(pyridin-3-yl)azo]pyridine as well as the salts thereof. Particularly preferred among the aforesaid direct dyes are the following compounds, alone or in combination with one another: hydroxyethyl-2-nitro-p-toluidine, 2-hydroxyethylpicramic acid, 4-nitrophenylaminourea, tri(4-amino-3-methylphenyl)carbenium chloride (Basic Violet 2), 1,4-di-amino-9,10-anthracenedione (Disperse Violet 1), 1-(2-hydroxy-ethyl)amino-2-nitro-4-[di(2-hydro-xyethyl)amino]benzene (HC Blue No. 2), 4-[ethyl-(2-hydroxyethyl)amino]-1-[(2-hydroxyethyl)amino]-2-nitrobenzene hydrochloride (HC Blue No. 12), 1-amino-4-[di(2-hydroxyethyl)amino]-2-nitrobenzene hydrochloride (HC Red No. 13), 4-amino-1-[(2-hydroxyethyl)amino]-2-nitrobenzene (HC Red No. 3), 4-amino-3-nitrophenol, 4-[(2-hydroxyethyl)amino]-3-nitrophenol, 1-amino-5-chloro-4-[(2,3-dihydroxypropyl)amino]-2-nitrobenzene (HC Red No. 10), 5-chloro-1,4-[di(2,3-dihydroxypropyl)-amino]-2-nitrobenzene (HC Red No. 11), 2-chloro-6-ethylamino-4-nitrophenol, 2-amino-6-chloro-4-nitrophenol, 4-[(2-hydroxyethyl)amino]-3-nitro-1-trifluoromethylbenzene (HC Yellow No. 13), 8-amino-2-bromo-5-hydroxy-4-imino-6-{[3-(trimethylammonio)-phenyl]amino}-1(4H)-naphthalenone chloride (C.I. 56059; Basic Blue No. 99), 1-[(4-aminophenyl) azo]-7-(trimethylammonio)-2-naphthol chloride (C.I. 12250; Basic Brown No. 16), 1-[(4-amino-2-nitrophenyl) azo]-7-(trimethylammonio)-2-naphthol chloride (Basic Brown No. 17), 2-hydroxy-1-[(2-methoxyphenyl)azo]-7-(trimethylammonio)naphthalene chloride (C.I. 12245; Basic Red No. 76), 3-methyl-1-phenyl-4-{[3-(trimethylammonio) phenyl]azo}pyrazol-5-one chloride (C.I. 12719; Basic Yellow No. 57) and 2,6-diamino-3-[(pyridin-3-yl)azo]pyridine as well as the salts thereof.

In at least one embodiment, the composition comprises from 0.1 wt.-% to 15 wt.-%, preferably from 0.1 wt.-% to 10 wt.-%, even more preferably from 0.5 wt.-% to 8.0 wt.-% of at least one direct dye.

In at least one embodiment, the composition comprises a perfume or fragrance ingredient. Individual fragrance compounds, e.g. the synthetic products of the type of esters, ethers, aldehydes, ketones, alcohols and hydrocarbons can be used as fragrance or perfume oils. Fragrance compounds of the ester type are e.g. benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl-methylphenyl glycinate, allylcyclohexyl propionate, styrallyl propionate and benzyl salicylate. The ethers include for example benzyl ethyl ether, the aldehydes include e.g. the linear alkanals with 8 to 18 carbon atoms, citral, citronellal, citronellyloxyacetaldehyde, cyclamen aldehyde, hydroxycitronellal, ilial and bourgeonal, the ketones include e.g. the ionones, alpha-isomethylionone and methyl-cedryl ketone, the alcohols include anethole, citronellol, eugenol, geraniol, linalool, phenylethyl alcohol and terpineol, and the hydrocarbons include mainly the terpenes and balsams. Preferably, mixtures of various fragrances are used, which together produce an attractive perfume note. Perfume oils can also contain mixtures of natural odoriferous substances that can be obtained from vegetable or animal sources, e.g. pine oil, citrus oil, jasmine oil, lily oil, rose oil, or ylang-ylang oil. Essential oils of lower volatility, which are used mostly as flavor components, are also suitable as perfume oils, e.g. sage oil, chamomile oil, clove oil, melissa oil, mint oil, cinnamon leaf oil, linden flower oil, juniper berry oil, vetiver oil, olibanum oil, galbanum oil and labdanum oil. In at least one embodiment, the composition comprises from 0.01 wt.-% to 3.0 wt.-%, preferably from 0.05 wt.-% to 2.0 wt.-%, even more preferably from 0.1 wt.-% to 1.0 wt.-% of at least one perfume or fragrance ingredient.

In at least one embodiment, the composition comprises a carrier, solvent or diluent. In at least one embodiment, the composition comprises a solvent, wherein the solvent comprises water and/or alcohol. Solvent is useful for providing the compounds used in present invention in liquid form. In at least one embodiment, the solvent is cosmetically acceptable. In at least one embodiment, the composition comprises at least 10 wt.-% water. Water is useful for economic reasons but also because it is cosmetically acceptable. Optionally the composition comprises water-miscible or water-soluble solvents such as lower alkyl alcohols. In at least one embodiment, the composition comprises $C_1$-$C_5$ alkyl monohydric alcohols, preferably $C_2$-$C_3$ alkyl alcohols. The alcohols which may be present in particular lower monohydric or polyhydric alcohols having 1 to 4 carbon atoms customarily used for cosmetic purposes, such as preferably ethanol and isopropanol. Optionally, the composition comprises a water-soluble polyhydric alcohol. In at least one embodiment, the water-soluble polyhydric alcohols are polyhydric alcohols having two or more hydroxyl groups in the molecule. In at least one embodiment, the water-soluble polyhydric alcohol is selected from the group consisting of: dihydric alcohols such as ethylene glycol, propylene glycol, trimethylene glycol, 1,2-butylene glycol, 1,3-butylene glycol, 1,4-butylene glycol, tetramethylene glycol, 2,3-butylene glycol, pentamethylene glycol, 2-butene-1,4-diol, hexylene glycol, octylene glycol; trihydric alcohols such as glycerine, trimethylol propane, 1,2,6-hexanetriol and the like; tetrahydric alcohols such as penthaerythritol; pentahydric alcohols such as xylytol, etc.; hexahydric alcohols such as sorbitol, mannitol; polyhydric alcohol polymers such as diethylene glycol, dipropylene glycol, polyethylene glycol, polypropylene glycol, tetraethylene glycol, diglycerine, polyethylene glycol, triglycerine, tetraglycerine, polyglycerine; dihydric alcohol alkyl ethers such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether; dihydric alcohol alkyl ethers such as diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether; dihydric alcohol ether esters such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate; glycerine monoalkyl ethers such as xyl alcohol, selachyl alcohol, batyl alcohol; sugar alcohols such as sorbitol, maltitol, maltotriose, mannitol, sucrose, erythritol, glucose, fructose, starch sugar, maltose, xylytose, starch sugar reduced alcohol, glysolid, tetrahydrofurfuryl alcohol, POE tetrahydrofurfuryl alcohol, POP butyl ether, POP POE butyl ether, tripolyoxypropylene glycerine ether, POP glycerine ether, POP glycerine ether phosphoric acid, POP POE pentanerythritol ether, and mixtures thereof. In a preferred embodiment, the composition comprises a solvent selected from the group consisting of water, glycols, ethanol, and combinations thereof. In a preferred embodiment, the composition comprises an aqueous, alcoholic or aqueous-alcoholic solvent, and wherein the aqueous, alcoholic or aqueous-alcoholic solvent comprises water, ethanol, propanol, isopropanol, 1,2-propylene glycol, 1,3-propylene glycol, isobutanol, butanol, butyl glycol, butyl diglycol, glycerol, or a mixture thereof; preferably wherein the aqueous, alcoholic or aqueous-alcoholic solvent comprises water, ethanol, propanol, isopropanol, 1,2-propylene glycol, 1,3-propylene glycol, glycerol, or mixtures thereof; more preferably wherein the aqueous, alcoholic or aqueous-alcoholic solvent comprises water, isopropanol, 1,2-propylene glycol, 1,3-propylene glycol, or mixtures thereof; even more preferably wherein the aqueous, alcoholic or aqueous-alcoholic solvent consists of water or consists of a mixture of water and an alcohol wherein the alcohol is selected from the group consisting of isopropanol, 1,2-propylene glycol and 1,3-propylene glycol. Natural solvents can also be used. In at least one embodiment, the composition comprises a solvent selected from the group consisting of plant oil, honey, plant-derived sugar compositions, and mixtures thereof. In at least one embodiment, the composition comprises from 0.5 wt.-% to 90 wt.-%, preferably from 1.0 wt.-% to 80 wt.-%, even more preferably from 5.0 wt.-% to 70 wt.-% of at least one carrier, solvent and/or diluent.

In at least one embodiment, the composition comprises a propellant. In at least one embodiment, the propellant is selected from compressed gas propellants and liquefied gas propellants. In at least one embodiment, the compressed gas propellants are selected from the group consisting of air, nitrogen (N2), nitrous oxide (N20), carbon dioxide (C02), and mixtures thereof; preferably air, nitrogen (N2), and mixtures thereof; most preferably nitrogen (N2). In at least one embodiment, the liquefied gas propellants are selected from the group consisting of dimethylether (DME), 1,1-difluoroethane (HFC-152a), 1,1,1,2-tetrafluoroethane (HFC-134a), pentane, n-butane, iso-butane, propane, trans-1,3,3,3-tetrafluoropropene (HFO-1234ze), and mixtures thereof, preferably dimethylether (DME), 1,1-difluoroethane (HFC-152a), and mixtures thereof. In a preferred embodiment, the propellant is selected from the group consisting of nitrogen, carbon dioxide, pentane, n-butane, iso-butane, propane, and combinations thereof. In at least one embodiment, the composition comprises from 0.5 wt.-% to 60 wt.-%, preferably from 1.0 wt.-% to 50 wt.-%, even more preferably from 2.0 wt.-% to 40 wt.-% of at least one propellant.

In at least one embodiment, the composition comprises a functional acid or an active ingredient. Functional acids and active ingredients are substances used to impart a clinical functionality to the skin or hair upon application. Functional acids and active ingredients are for example used as exfoliants, skin-brightening agents, self-tanning agents, anti-acne agents and anti-ageing agents. In another preferred embodiment of the invention, the compositions according to the invention contain one or more hydroxy acids, especially preferably one or more substances selected from alpha- and beta-hydroxy acids. The compositions according to the invention can contain, as hydroxy acids, preferably lactic acid, glycolic acid, salicylic acid and alkylated salicylic acids or citric acid. Furthermore, formulations according to the invention can contain other acidic components. Consideration may be given to the following as active ingredient: tartaric acid, mandelic acid, caffeic acid, pyruvic acid, oligo-oxa mono- and dicarboxylic acids, fumaric acid, retinoic acid, sulfonic acids, benzoic acid, kojic acid, fruit acid, malic acid, gluconic acid, pyruvic acid, galacturonic acid, ribonic acid, hyaluronic acid, and all derivatives thereof, polyglycol diacids in free or partial neutralized form, vitamin C (ascorbic acid), vitamin C derivatives (e.g. sodium ascorbyl phosphate, magnesium ascorbyl phosphate and magnesium ascorbyl glucoside), dihydroxyacetone, minoxidil, proteolytic enzymes (e.g. fruit enzymes from papaya, pumpkin and pineapple such as papainase and bromelin ananase), caffeine, niacinamide and its derivatives, diethyl toluamide (DEET), or skin-whitening actives such as arbutin or glycyrrhetic acid and salts thereof, glutathione, cysteine, resveratrol, 4-butylresorcinol, or plant extracts like pancratium maritimum extract or mulberry extract. In a preferred embodiment, the functional acid and/or an active ingredient is selected from the group consisting of salicylic acid, kojic acid, hyaluronic acid, ascorbic acid, and all derivatives thereof, dihydroxyacetone, arbutin, and combinations thereof. In at least one embodiment, the composition comprises from 0.05 wt.-% to 15 wt.-%, preferably from 0.1 wt.-% to 10 wt.-%, even more preferably from 0.5 wt.-% to 5.0 wt.-% of at least one functional acid or/and an active ingredient.

In at least one embodiment, the composition comprises a deodorant or an anti-perspirants. In at least one embodiment, the composition comprises a deodorising agent. In at least one embodiment, the deodorising agent is selected from the group consisting of allantoin, bisabolol, and combinations thereof. In at least one embodiment, the composition comprises from 0.001 wt.-% to 10 wt.-%, or from 0.01 wt.-% to 9.0 wt.-%, or from 0.05 wt.-% to 8.0 wt.-%, or from 0.1 wt.-% to 5.0 wt.-% of at least one deodorising agent. The composition may comprise an antiperspirant. As antiperspirant it is possible to use aluminium chloride, aluminum chloride hydroxide, aluminum chloride dihydroxide, aluminum chlorohydrex polyethylene glycol complex, magnesium zirconium complexes or aluminum zirconium chloride hydroxide, for example. In at least one embodiment, the composition comprises from 0.001 wt.-% to 10 wt.-%, or from 0.01 wt.-% to 9.0 wt.-%, or from 0.05 wt.-% to 8.0 wt.-%, or from 0.1 wt.-% to 5.0 wt.-% of at least one antiperspirant.

In at least one embodiment, the composition comprises at least one viscosity modifier or thickening and/or gelling agent. The desired viscosity and rheology profile of the compositions can be adjusted by adding further thickeners and gelling agents. The viscosity-modifying substance is preferably a thickening polymer. In at least one embodiment, the thickening polymer selected from the group consisting of: copolymers of at least one first monomer type, which is chosen from acrylic acid and methacrylic acid, and at least one second monomer type, which is chosen from esters of acrylic acid and ethoxylated fatty alcohol, crosslinked polyacrylic acid, crosslinked copolymers of at least one first monomer type, which is chosen from acrylic acid and methacrylic acid, and at least one second monomer type, which is chosen from esters of acrylic acid with $C_{10}$- to $C_{30}$-alcohols; copolymers of at least one first monomer type, which is chosen from acrylic acid and methacrylic acid, and at least one second monomer type, which is chosen from esters of itaconic acid and ethoxylated fatty alcohol; copolymers of at least one first monomer type, which is chosen from acrylic acid and methacrylic acid, at least one second monomer type, which is chosen from esters of itaconic acid and ethoxylated $C_{10}$- to $C_{30}$-alcohol and a third monomer type, chosen from $C_1$-to $C_4$-aminoalkyl acrylates; copolymers of two or more monomers chosen from acrylic acid, methacrylic acid, acrylic esters and methacrylic esters; copolymers of vinylpyrrolidone and ammonium acryloyldimethyltaurate; copolymers of ammonium acryloyldimethyltaurate and monomers chosen from esters of methacrylic acid and ethoxylated fatty alcohols, hydroxyethylcellulose, hydroxypropylcellulose, hydroxypropylguar, glyceryl polyacrylate, glyceryl polymethacrylate, copolymers of at least one $C_2$-, $C_3$- or $C_4$-alkylene and styrene, polyurethanes, hydroxypropyl starch phosphate, polyacrylamide, copolymer of maleic anhydride and methyl vinyl ether crosslinked with decadiene, carob seed flour, gums such as guar gum, karaya gum, xanthan gum or dehydroxanthan gum, carrageenan, hydrolyzed corn starch; copolymers of polyethylene oxide, fatty alcohols and saturated methylenediphenyl diisocyanate (e.g. PEG-150/stearyl alcohol/SMDI copolymer), and mixtures thereof. In a preferred embodiment, the viscosity modifier or thickening and/or gelling agent is selected from the group consisting of carbomers, acrylates copolymers, xanthan gum, hydroxyethylcellulose, laureth-2, and combinations thereof. In at least one embodiment, the composition comprises from 0.01 wt.-% to 15 wt.-%, preferably from 0.1 wt.-% to 10 wt.-%, even more preferably from 0.5 wt.-% to 5.0 wt.-% of at least one viscosity modifier or thickening and/or gelling agent.

In at least one embodiment, the composition comprises an alkalizing agent or pH adjusting agent. In at least one embodiment, ammonia or caustic soda is suitable, but water-soluble, physiologically tolerable salts of organic and inorganic bases can also be considered. Optionally, the pH adjusting agent is selected from ammonium hydrogen carbonate, ammonia, monoethanolamine, ammonium hydroxide, ammonium carbonate. In at least one embodiment, the alkalizing agents is selected from the group consisting of 2-amino-2-methyl-1-propanol, 2-amino-2-methyl-1,3-propanediol, 2-amino-2-ethyl-1,3-propanediol, tris(hydroxylmethyl)-aminomethane, 2-amino-1-butanole, tris-(2-hydroxypropyl)-amine, 2,2-iminobisethanol, lysine, iminourea (guanidine carbonate), tetrahydro-1,4-oxazine, 2-amino-5-guanidin-valeric acid, 2-aminoethansulfonic acid, diethanolamine, triethanolamine, N-methyl ethanolamine, isopropanolamine, diisopropanolamine, triisopropanolamine, glucamine, sodium hydroxide, potassium hydroxide, lithium hydroxide and magnesium oxide, and mixtures thereof. To establish an acidic pH value, and acid can be included. In at least one embodiment, the composition comprises an acid selected from the group consisting of hydrochloric acid, phosphoric acid, acetic acid, formic acid, sulfuric acid, hydrochloric acid, citric acid, ascorbic acid, and mixtures thereof. Citric acid is most preferred in that it has high consumer acceptance. In at least one embodiment, the acidic pH is adjusted with a buffer such as a phosphate buffer, a TRIS buffer or a citric buffer. The buffers may be used alone or in combination with an acid. In a preferred embodiment, the alkalizing or pH adjusting agent is selected from the group consisting of triethanolamine, sodium hydroxide, lactic acid, citric acid, and combinations thereof. In at least one embodiment, the composition comprises from 0.001 wt.-% to 5.0 wt.-%, preferably from 0.01 wt.-% to 3.0 wt.-%, even more preferably from 0.1 wt.-% to 1.0 wt.-% of at least one alkalizing or pH adjusting agent.

In at least one embodiment, the composition/formulation comprises an anti-oxidant. In at least one embodiment, the anti-oxidant is selected from the group consisting of amino acids, peptides, sugars, imidazoles, carotinoids, carotenes, chlorogenic acid, lipoic acid, thiols, thiol glycosyl esters, thiol N-acetyl esters, thiol methyl esters, thiol ethyl esters, thiol propyl esters, thiol amyl esters, thiol butyl esters, thiol lauryl esters, thiol palmitoyl esters, thiol oleyl esters, thiol linoleyl esters, thiol cholesteryl esters, thiol glyceryl esters, dilaurylthiodipropionate, distearylthiodipropionate, thiodipropionic acid, metal chelators, hydroxy acids, fatty acids, folic acids, vitamin C, tocopherol, vitamin A, stilbenes, derivatives and combinations thereof. In at least one embodiment, the anti-oxidant is selected from the group consisting of glycine, histidine, tyrosine, tryptophan, urocaninic acid, D,L-carnosine, D-carnosine, L-carnosine, beta-carotene, alpha-carotene, lycopene, dihydrolipoic acid, aurothioglucose, propylthiouracil, thioredoxine, glutathione, cysteine, cystine, cystamine, buthioninsulfoximine, homocysteinsulfoximine, buthioninsulfone, penta-, hexa-, heptathioninsulfoximine, hydroxyfatty acids, palmitic acid, phytinic acid, lactoferrin, citric acid, lactic acid, malic acid, humic acid, bile acid, bilirubin, biliverdin, EDTA, EGTA, linoleic acid, linolenic acid, oleic acid, butylhydroxyanisol, trihydroxybutyrophenone, ubichinon, ubichinol, ascorbylpalmitate, Mg-ascorbylphosphate, ascorbylacetate, vitamin E acetate, vitamin A palmitate, carnosine, mannose, ZnO, $ZnSO_4$, selenium methionine, stilbenes, superoxide dismutase, and combinations thereof. In at least one embodiment, the antioxidant is selected from the group consisting of vitamin A, vitamin A derivatives, vitamin E, vitamin E derivatives, and combinations thereof. In at least one embodiment, the composition comprises from 0.001 wt.-% to 10 wt.-%, preferably from 0.05 wt.-% to 5.0 wt.-%, even more preferably from 0.1 wt.-% to 3.0 wt.-%, most preferably from 0.05 wt.-% to 1.0 wt.-% of at least one antioxidant.

In at least one embodiment, the composition/formulation comprises a chelant. In at least one embodiment, the chelant is selected from the group consisting of EDTA, caprylhydroxamic acid, oxalate derivatives, disodium hydroxyethyliminodiacetate, galacturonic acid and derivatives, glucuronic acid and derivatives, lauroyl ethylenediamine triacetic acid, methyl dihydroxybenzoate, trisodium ethylenediamine disuccinate, phytic acid, itaconic acid, propane tricarboxylic acid, citric acid and derivatives (e.g. diammonium citrate, bismuth citrate and acetyl trihexyl citrate 2,6-dicarboxy pyridine), phosphoric and phosphonic acid derivatives (e.g. diethylenetriamine pentamethylene phosphonic acid, disodium azacycloheptane diphosphonate, glycereth-26 phosphate, disodium pyrophosphate, disodium salicylphosphate, aminotrimethylene phosphonic acid, phosphonobutanetricarboxylic acid, potassium trisphosphonomethylamine oxidebeta-alanine diacetic acid or cyclohexanediamine tetraacetic acid). In at least one embodiment, the chelant is selected from the group consisting EDTA, oxalate derivatives, disodium salicylphosphate, and combinations thereof. In at least one embodiment, the composition comprises from 0.01 wt.-% to 2.0 wt.-%, preferably from 0.05 wt.-% to 1.5 wt.-%, even more preferably from 0.1 wt.-% to 1.0 wt.-%, most preferably from 0.05 wt.-% to 1.0 wt.-% of at least one chelant.

In at least one embodiment, the composition comprises an astringent. In at least one embodiment, the astringent is selected from the group consisting of magnesium oxide, aluminium oxide, titanium dioxide, zirconium dioxide, zinc oxide, oxide hydrates, aluminium oxide hydrate (boehmite) and hydroxide, chlorohydrates of calcium, magnesium, aluminium, titanium, zirconium or zinc. In at least one embodiment, the composition comprises from 0.001 wt.-% to 10 wt.-%, or from 0.01 wt.-% to 9.0 wt.-%, or from 0.05 wt.-% to 8.0 wt.-%, or from 0.1 wt.-% to 5.0 wt.-% of at least one astringent.

In at least one embodiment, the composition comprises a sun protection agent and/or UV filter. Suitable sun protection agents and UV filters are disclosed in WO2013017262A1 (published on 7 Feb. 2013), from page 32, line 11 to the end of page 33. The photoprotective substances include, in particular, all of the photoprotective substances specified in EP1084696A1, which is incorporated herein by reference. In another preferred embodiment of the invention, the compositions according to the invention contain one or more substances selected from inorganic and organic UV filters and especially preferably are in the form of sunscreen compositions.

The compositions according to the invention can contain microfine titanium dioxide, mica-titanium oxide, iron oxides, mica-iron oxide, zinc oxide, silicon oxides, ultramarine blue or chromium oxides as pigments/micropigments and as inorganic sunscreen filters or UV filters. The organic sunscreen filters or UV filters are preferably selected from 4-aminobenzoic acid, 3-(4'-trimethylammonium)-benzylidene-bornan-2-one-methylsulfate, camphor benzalkonium methosulfate, 3,3,5-trimethyl-cyclohexylsalicylate, 2-hydroxy-4-methoxybenzophenone, 2-phenylbenzimidazole-5-sulfonic acid and their potassium, sodium and triethanolamine salts, 3,3'-(1,4-phenylenedimethine)-bis(7,7-dimethyl-2-oxobicyclo[2.2.1]-heptane-1-methanesulfonic acid) and salts thereof, 1-(4-tert-butylphenyl)-3-(4-methoxyphenyl)propane-1,3-dione, 3-(4'-sulfo)-benzylidene-bornan-2-one and salts thereof, 2-cyano-3,3-diphenylacrylic acid-(2-ethylhexyl ester), polymers of N-[2(and 4)-(2-oxoborn-3-ylidenemethyl)benzyl]-acrylamide, 4-methoxy-cinnamic acid-2-ethylhexyl ester, ethoxylated ethyl-4-aminobenzoate, 4-methoxy-cinnamic acid isoamyl ester, 2,4,6-tris-[p-(2-ethylhexyloxycarbonyl)anilino]-1,3,5-triazine, 2-(2H-benzotriazol-2-yl)-4-methyl-6-(2-methyl-3-(1,3,3,3-tetramethyl-1-(trimethylsilyloxy)-disiloxanyl)-propyl)phenol, 4,4'-[(6-[4-((1,1-dimethylethyl)-aminocarbonyl)phenylamino]-1,3,5-triazin-2,4-yl)diimino] bis-(benzoic acid-2-ethylhexyl ester), benzophenone-3, benzophenone-4 (acid), 3-(4'-methylbenzylidene)-D,L-camphor, 3-benzylidene-camphor, salicylic acid-2-ethylhexyl ester, 4-dimethylaminobenzoic acid-2-ethylhexyl ester, hydroxy-4-methoxy-benzophenone-5-sulfonic acid (sulfisobenzonum) and the sodium salt, 4-isopropylbenzylsalicylate, N,N,N-trimethyl-4-(2-oxoborn-3-ylidenemethyl) anilium methyl sulfate, homosalate (INN), oxybenzone (INN), 2-phenylbenzimidazole-5-sulfonic acid and their sodium, potassium, and triethanolamine salts, octylmethoxycinnamic acid, isopentyl-4-methoxycinnamic acid, isoamyl-p-methoxycinnamic acid, 2,4,6-trianilino-(p-carbo-2'-ethylhexyl-1'-oxy)-1,3,5-triazine (octyl triazone) phenol, 2-2(2H-benzotriazol-2-yl)-4-methyl-6-(2-methyl-3-(1,3,3,3-tetramethyl-1-(trimethylsilyl)oxy)-disiloxanyl)propyl (drometrizole trisiloxane) benzoic acid, 4,4-((6-(((1,1-dimethylethyl)amino)carbonyl)phenyl)amino)-1,3,5-triazine-2,4-diyl)diimino)bis,bis(2-ethylhexyl)ester) benzoic acid, 4,4-((6-(((1,1-dimethylethyl)amino)-carbonyl)phenyl)amino)-1,3,5-triazine-2,4-diyl)diimino)bis,bis(2-ethylhexyl)ester), 3-(4'-methylbenzylidene)-D,L-camphor (4-methylbenzylidene camphor), benzylidene-camphor-sulfonic acid, octocrylene, polyacrylamidomethyl-benzylidene-camphor, 2-ethylhexyl salicylate (octyl salicylate), 4-dimethyl-aminobenzoic acid ethyl-2-hexyl ester (octyl dimethyl PABA), PEG-25 PABA, 2-hydroxy-4-methoxybenzophenone-5-sulfonic acid (benzophenone-5) and the Na salt, 2,2'-methylene-bis-6-(2H-benzotriazol-2-yl)-4-(tetramethylbutyl)-1,1,3,3-phenol, sodium salt of 2-2'-bis-(1,4-phenylene)1H-benzimidazole-4,6-disulfonic acid, (1,3,5)-triazine-2,4-bis((4-(2-ethylhexyloxy)-2-hydroxy)-phenyl)-6-(4-methoxyphenyl), 2-ethylhexyl-2-cyano-3,3-diphenyl-2-propenoate, glyceryl octanoate di-p-methoxycinnamic acid, p-amino-benzoic acid and esters thereof, 4-tert-butyl-4'-methoxydibenzoylmethane, 4-(2-β-glucopyranoxy) propoxy-2-hydroxybenzophenone, octyl salicylate, methyl-2,5-diisopropylcinnamic acid, cinoxate, dihydroxydimethoxybenzophenone, disodium salt of 2,2'-dihydroxy-4,4'-dimethoxy-5,5'-disulfobenzophenone, dihydroxybenzophenone, 1,3,4-dimethoxyphenyl-4,4-dimethyl-1,3-pentanedione, 2-ethylhexyl-dimethoxybenzylidene-dioxoimidazolidine propionate, methylene-bisbenzotriazolyl tetramethylbutylphenol, phenyldibenzimidazole tetrasulfonate, bis-ethylhexyloxyphenol-methoxyphenol-triazine, tetrahydroxybenzophenones, terephthalylidene-dicamphor-sulfonic acid, 2,4,6-tris[4,2-ethylhexyloxycarbonyl)anilino]-1,3,5-triazine, methyl-bis(trimethylsiloxy)silyl-isopentyl trimethoxycinnamic acid, amyl-p-dimethylaminobenzoate, amyl-p-dimethylaminobenzoate, 2-ethylhexyl-p-dimethylaminobenzoate, isopropyl-p-methoxycinnamic acid/diisopropylcinnamic acid ester, 2-ethylhexyl-p-methoxycinnamic acid, 2-hydroxy-4-methoxybenzophenone, 2-hydroxy-4-methoxybenzophenone-5-sulfo acid and the trihydrate, and 2-hydroxy-4-methoxybenzophenone-5-sulfonate sodium salt, phenylbenzimidazole-sulfonic acid, p-aminobenzoic acid butyl ester, methyl-3-[2,4-bis(methylethyl)phenyl]-2-propenoate, 3-(4-hydroxy)-3-methoxyphenyl)-2-propenoic acid, 5-methyl-2-(1-methylethyl)cyclohexanol-2-aminobenzoate, diethylmalonylbenzylidene oxypropene dimethicone, 2,4,6-tris(biphenyl-4-yl)-1,3,5-triazin and tris(2-hydroxyethyl) ammonium 2-hydroxybenzoate. In a preferred embodiment, the sun protection agent and/or UV filter is selected from the group consisting of 2-ethylhexyl 4-methoxycinnamate, methyl methoxycinnamate, 2-ethylhexyl salicylate, 2-ethylhexyl-2-cyano-3,3-diphenyl-2-propenoate, 2-hydroxy-4-methoxybenzophenone-5-sulfonic acid, polyethoxylated p-aminobenzoates, and combinations thereof. In at least one embodiment, the composition comprises from 0.001 wt.-% to 30 wt.-%, preferably from 0.05 wt.-% to 20 wt.-%, even more preferably from 0.1 wt.-% to 10 wt.-%, most preferably from 0.05 wt.-% to 5.0 wt.-% of at least one sun protection agent and/or UV filter.

In at least one embodiment, the composition comprises a skin conditioning agent. Skin conditioning agents such as emollients, humectants and occlusive agents are ingredients which help to maintain the soft and smooth appearance of the skin or which help to improve the condition of dry or damaged skin. In at least one embodiment, the skin conditioning agent is selected from the group consisting of oily substances (description see above), functional acids or active ingredients (description see above), fatty acid N-alkylpolyhydroxyalkyl amides, fatty acids, triglycerides, panthenol, allantoin, bisabolol, glycerol, sorbitol, urea and derivatives thereof, trehalose, erythrulose, pyrrolidone carboxylic acid (PCA) and its salts, polyglucuronic acid, gluconolactone, petrolatum, ubichinon-10 and ubiquinol. In a preferred embodiment, the skin conditioning agent is selected from the group consisting of urea, glycerine, pyrrolidone carboxylic acid (PCA) and its salts, panthenol, petrolatum, and combinations thereof. In at least one embodiment, the composition comprises from 0.001 wt.-% to 5.0 wt.-%, preferably from 0.05 wt.-% to 3.0 wt.-%, even more preferably from 0.1 wt.-% to 1.0 wt.-% of at least one skin conditioning agent.

In at least one embodiment, the composition comprises an anti-foaming agent. Antifoams are chemicals which reduce the tendency of finished products to generate foam on shaking or agitation. In at least one embodiment, the anti-foaming agent is selected from the group consisting of alcohols (e.g. ethanol, isopropyl alcohol or propyl alcohol), alkoxylated alcohols (e.g. laureth-5 butyl ether), silicon oils and resins (e.g. dimethicone and its derivatives such as cetyl dimethicone, phenyl dimethicone, PEG/PPG-12/18 dimethicone and hydrogen trifluoropropyl dimethicone, trimethylsiloxysilicate/dimethicone crosspolymer or polysilicone-10) and hydrophobic silica derivatives (e.g. silica silylate). In a preferred embodiment, the anti-foaming agent is selected from the group consisting of ethanol, dimethicone, silica silylate, and combinations thereof. In at least one embodiment, the composition comprises from 0.01 wt.-% to 5.0 wt.-%, preferably from 0.1 wt.-% to 3.0 wt.-%, even more preferably from 0.5 wt.-% to 2.0 wt.-% of at least one anti-foaming agent.

In at least one embodiment, the composition comprises a flavouring agent. In at least one embodiment, the flavouring agent is selected from the group consisting of 1-acetonaphthalene, 1-decen-3-ol, p-methylbenzaldehyde, p-propenylphenyl methyl ether, aspartame, benzaldehyde, bromocinnamal, calcium cyclohexylsulfamate, calcium o-benzolufimide, carvone, cinnamic aldehyde, 3,7-dimethyl-6-octenoic acid, fruit sugar, glucose, glucosyl stevioside, honey, 3-methyl-1-butanol, 4-hydroxy-3-methoxy-1-propenylbenzene, malt sugar, menthol, eucalyptol, thymol, potassium 6-methyl-1,2,2-oxathiazin-4(3H)-one 2,2'-dioxide, isodulcitol, saccharine, stevioside, 1',4,6'-trichloro-galacto-sucrose, sorbitol, saccharose, sodium saccharin, methyl salicylate vanillaldehyde, xylite, xylose and plant extracts. In a preferred embodiment, the flavouring agent is selected from the group consisting of benzaldehyde, cinnamic aldehyde, fruit sugar, stevioside and its derivatives, saccharine, saccharose, vanillaldehyde, xylite, and combinations thereof. In at least one embodiment, the composition comprises from 0.001 wt.-% to 3.0 wt.-%, preferably from 0.01 wt.-% to 2.0 wt.-%, even more preferably from 0.05 wt.-% to 1.0 wt.-% of at least one flavouring agent.

In at least one embodiment, the composition comprises an electrolyte. In at least one embodiment, the electrolyte is selected from the group consisting of salts preferably ammonium or metal salts, especially preferably halides, for example $CaCl_2$, $MgCl_2$, LiCl, KCl and NaCl, carbonates, hydrogen carbonates, phosphates, sulfates, nitrates, especially preferably sodium chloride, sodium fluoride, sodium monofluorophosphate, stannous fluoride, and/or organic salts, preferably ammonium or metal salts, especially preferably of glycolic acid, lactic acid, citric acid, tartaric acid, mandelic acid, salicylic acid, ascorbic acid, pyruvic acid, fumaric acid, retinoic acid, sulfonic acids, benzoic acid, kojic acid, fruit acid, malic acid, gluconic acid or galacturonic acid. These also include aluminum salts, preferably aluminum hydrochloride or aluminum-zirconium complex salts. In a preferred embodiment of the invention the compositions according to the invention therefore contain one or more substances selected from inorganic and organic salts. As electrolyte, the compositions according to the invention can also contain mixtures of various salts. In a preferred embodiment, the electrolyte is selected from the group consisting of sodium chloride, magnesium chloride, sodium citrate, sodium acetate, sodium hyaluronate, and combinations thereof. In at least one embodiment, the composition comprises from 0.001 wt.-% to 5.0 wt.-%, preferably from 0.05 wt.-% to 3.0 wt.-%, even more preferably from 0.1 wt.-% to 1.0 wt.-% of at least one electrolyte.

In at least one embodiment, the composition comprises an oxidizing or reducing agent. In at least one embodiment, the oxidizing or reducing agent is selected from the group consisting of ammonium persulfate, calcium peroxide, hydrogen peroxide, hypochlorous acid, sodium hypochlorite, potassium monopersulfate, sodium carbonate peroxide, ammonium thioglycolate, cysteine, glutathione, hydroquinone, mercaptopropionic acid, superoxide dismutase, thioglycerin, thioglycolic acid, thiolactic acid, sodium sulfite, sodium thioglycolate, potassium thioglycolate, cysteine, the compositions according to the invention can also contain mixtures of various agents. In a preferred embodiment, the oxidizing or reducing agent is selected from the group consisting of hydrogen peroxide, sodium hypochlorite, superoxide dismutase, thioglycolic acid, sodium thioglycolate, potassium thioglycolate, cysteine, sodium carbonate peroxide, and combinations thereof. In at least one embodiment, the composition comprises from 0.001 wt.-% to 10 wt.-%, preferably from 0.05 wt.-% to 7.0 wt.-%, even more preferably from 0.1 wt.-% to 5.0 wt.-% of at least one oxidizing or reducing agent.

Composition Properties

In at least one embodiment, the composition has a viscosity of from 0 cPs to 20,000 cPs. In at least one embodiment, the composition has a viscosity of from 0.1 cPs to 10,000 cPs, or from 1 cPs to 5,000 cPs, or from 5 cPs to 3,500 cPs. The viscosity measurement conditions are defined in the definitions section above. Viscosity may be important for anti-drip reasons. Dripping can be inconvenient for the user. Furthermore, more viscous compositions can be useful for measured dispensing. In at least one embodiment, the composition has a viscosity of from 0 cPs to 1,000 cPs. This viscosity range is advantageous when the composition is in the form of a facial cleanser in view of the need for distribution on skin and ability to rinse off.

In at least one embodiment, the composition further comprises a viscosity-modifying substance. The viscosity-modifying substance is preferably a thickening polymer. In at least one embodiment, the thickening polymer selected from the group consisting of: copolymers of at least one first monomer type, which is chosen from acrylic acid and methacrylic acid, and at least one second monomer type, which is chosen from esters of acrylic acid and ethoxylated fatty alcohol; crosslinked polyacrylic acid; crosslinked copolymers of at least one first monomer type, which is chosen from acrylic acid and methacrylic acid, and at least one second monomer type, which is chosen from esters of acrylic acid with $C_{10}$- to $C_{30}$-alcohols; copolymers of at least one first monomer type, which is chosen from acrylic acid and methacrylic acid, and at least one second monomer type, which is chosen from esters of itaconic acid and ethoxylated fatty alcohol; copolymers of at least one first monomer type, which is chosen from acrylic acid and methacrylic acid, at least one second monomer type, which is chosen from esters of itaconic acid and ethoxylated $C_{10}$- to $C_{30}$-alcohol and a third monomer type, chosen from $C_1$-to $C_4$-aminoalkyl acrylates; copolymers of two or more monomers chosen from acrylic acid, methacrylic acid, acrylic esters and methacrylic esters; copolymers of vinylpyrrolidone and ammonium acryloyldimethyltaurate; copolymers of ammonium acryloyldimethyltaurate and monomers chosen from esters of methacrylic acid and ethoxylated fatty alcohols; hydroxyethylcellulose; hydroxypropylcellulose; hydroxypropylguar; glyceryl polyacrylate; glyceryl polymethacrylate; copolymers of at least one $C_2$-, $C_3$- or $C_4$-alkylene and styrene; polyurethanes; hydroxypropyl starch phosphate; polyacrylamide; copolymer of maleic anhydride and methyl vinyl ether crosslinked with decadiene; carob seed flour; guar gum; xanthan; dehydroxanthan; carrageenan; karaya gum; hydrolyzed corn starch; copolymers of polyethylene oxide, fatty alcohols and saturated methylenediphenyl diisocyanate (e.g. PEG-150/stearyl alcohol/SMDI copolymer); and mixtures thereof.

In at least one embodiment, the composition has a pH value of from 2.0 to 12.0, preferably from 3.0 to 9.0, more preferably from 4.5 to 7.5. By varying the pH value, a composition can be made available that is suitable for different applications.

In at least one embodiment, the composition is in liquid form. In an alternative embodiment, the composition is in solid form. Optionally, the composition is in powdered or granulated form. This is advantageous in that it is not needed to ship the weight of liquid over long distances, which has economic and environmental benefits. A solid form can be achieved by spray drying the composition or the employment of a rotary evaporator. The composition can be converted into liquid form after it has been shipped e.g. by adding water. Clarity: Clear compositions are useful in view of increased consumer acceptance.

Composition Types

In at least one embodiment, the composition is a composition selected from the group consisting of hand dishwashing liquids, hard surface cleaners, and heavy duty laundry detergents. In at least one embodiment, the composition is a composition selected from the group consisting of water-based paints, hygiene compositions for use in hospitals (for cleaning and disinfecting), fungus treatments, pet or animal care compositions. In at least one embodiment, the composition is an ophthalmic product.

In at least one embodiment, the composition is a cosmetic composition.

In at least one embodiment, the composition is selected from the group consisting of shampoo, body wash, facial cleanser, face mask, bubble bath, intimate wash, bath oil, cleansing milk, micellar water, make-up remover, cleansing wipes, hair mask, perfume, liquid soap, shaving soap, shaving foam, cleansing foam, day cream, anti-ageing cream, body milk, body lotion, body mousse, face serum, eye cream, sunscreen lotion, sun cream, face cream, after-shave lotion, pre-shaving cream, depilatory cream, skin-whitening gel, self-tanning cream, anti-acne gel, mascara, foundation, primer, concealer, blush, bronzer, blemish balm (bb) cream, eyeliner, night cream, eye brow gel, highlighter, lip stain, hand sanitizer, hair oil, nail varnish remover, conditioner, hair styling gel, hair styling cream, anti-frizz serum, scalp treatment, hair colorant, split end fluid, deodorant, antiperspirant, baby cream, insect repellent, hand cream, sunscreen gel, foot cream, exfoliator, body scrub, cellulite treatment, bar soap, cuticle cream, lip balm, hair treatment, eye shadow, bath additive, body mist, eau de toilette, mouthwash, toothpaste, lubricating gel, moisturizer, serum, toner, aqua sorbet, cream gel, styling mousse, dry shampoo, lip stick, lip gloss, hydro-alcoholic gel, body oil, shower milk, illuminator, lip crayon, hair spray, combing cream, and sunblock.

Preferably, the composition is selected from the group consisting of shampoo, body wash, facial cleanser, face mask, bubble bath, cleansing milk, micellar water, make-up remover, cleansing wipes, hair mask, liquid soap, shaving soap, shaving foam, cleansing foam, day cream, anti-ageing cream, body milk, body lotion, body mousse, face serum, eye cream, sunscreen lotion, sun cream, face cream, after-shave lotion, pre-shaving cream, depilatory cream, skin-whitening gel, self-tanning cream, anti-acne gel, hair oil, conditioner, hair styling gel, hair styling cream, anti-frizz serum, scalp treatment, hair colorant, split end fluid, deodorant, antiperspirant, baby cream, insect repellent, hand cream, sunscreen gel, foot cream, exfoliator, body scrub, bar soap, hair treatment, mouthwash, toothpaste, moisturizer, serum, toner, aqua sorbet, cream gel, styling mousse, hydro-alcoholic gel, body oil, shower milk, hair spray, combing cream, and sunblock.

In at least one embodiment, the cosmetic, dermatological or pharmaceutical composition is for use on skin. In at least one embodiment, the composition is for use on the face, the neck, the body and/or around the eye area. In at least one embodiment, the composition is an emulsion or gel, preferably an oil-in-water (o/w), cream gel, hydro-alcoholic gel or hydrogel composition. In a preferred embodiment, the composition has a viscosity from 100 000 to 200 000 mPa·s, preferably from 1 000 to 100 000 mPa·s, even more preferably from 2 000 to 50 000 mPa·s and very preferably from 5 000 to 30 000 mPa·s (measured at 25° C., Brookfield RVT, T-C spindle at 20 revolutions per minute).

In at least one embodiment, the composition is a body or face care composition such as face creams, neck creams, body lotions, body milks, face serums, blemish balm creams, hand creams, foot creams, body butters, lip creams, eye creams, after-sun lotions, make-up removing lotions or body mists, diaper creams or baby lotions. Optionally the body or face care composition comprises from 0.1 wt.-% to 15 wt.-%, preferably from 0.5 wt.-% to 10 wt.-%, even more preferably from 1.0 wt.-% to 5.0 wt.-% of at least one emulsifier, coemulsifier and/or solubilizer. Emulsifiers, coemulsifiers and/or solubilizers are listed above. In at least one embodiment, the emulsifier, coemulsifier and/or solubilizer is selected from the group consisting of glyceryl stearate, cetearyl alcohol, polysorbate 20, stearic acid, cetearyl glucoside, PEG-40 hydrogenated castor oil, cetyl phosphate, steareth-2, ceteth-10 phosphate, trilaureth-4 phosphate, polyglyceryl-2 sesquiisostearate, cetyl PEG/PPG-10/1 dimethicone, and combinations thereof.

Optionally the body or face care composition comprises from 0.01 wt.-% to 40 wt.-%, preferably from 0.05 wt.-% to 30 wt.-%, even more preferably from 0.1 wt.-% to 20 wt.-% of at least one oily substance. Oily substances are listed above. In at least one embodiment, the oily substance is selected from the group consisting of sweet almond oil, argan oil, caprylic/capric triglyceride, dimethicone, squalane, apricot kernel oil, coconut oil, jojoba oil, shea butter, mineral oil, isopropyl isostearate, dicaprylyl carbonate, isohexadecane, and combinations thereof.

Optionally the body or face care composition comprises from 0.01 wt.-% to 20 wt.-%, preferably from 0.05 wt.-% to 10 wt.-%, even more preferably from 0.1 wt.-% to 5.0 wt.-% of at least one wax. Waxes are listed above. In at least one embodiment, the wax is selected from the group consisting of carnauba wax, beeswax, candelilla wax, synthetic wax, polyethylene, paraffin wax, microcrystalline wax, hydrogenated vegetable oil, hydrogenated castor oil, rice bran wax, cetyl dimethicone, and combinations thereof.

Optionally the body or face care composition comprises from 0.01 wt.-% to 15 wt.-%, preferably from 0.1 wt.-% to 10 wt.-%, even more preferably from 0.3 wt.-% to 5.0 wt.-% of at least one viscosity modifier or thickening and/or gelling agent. Viscosity modifiers or thickening and/or gelling agents are listed above. In at least one embodiment, the viscosity modifier or thickening and/or gelling agent is selected from the group consisting of carbomers, acrylates copolymers, xanthan gum, hydroxyethylcellulose, polyamides, and combinations thereof.

Optionally the body or face care composition comprises from 0.001 wt.-% to 5.0 wt.-%, preferably from 0.05 wt.-% to 3.0 wt.-%, even more preferably from 0.1 wt.-% to 1.0 wt.-% of at least one skin conditioning agent. Skin conditioning agents are listed above. In at least one embodiment, the skin conditioning agent is selected from the group consisting of urea, glycerine, pyrrolidone carboxylic acid (PCA) and its derivatives, panthenol, petrolatum, and combinations thereof.

Optionally the body or face care composition comprises from 0.001 wt.-% to 10 wt.-%, preferably from 0.05 wt.-% to 5.0 wt.-%, even more preferably from 0.1 wt.-% to 3.0 wt.-%, most preferably from 0.05 wt.-% to 1.0 wt.-% of at least one antioxidant. Antioxidants are listed above. In at least one embodiment, the antioxidant is selected from the group consisting of vitamin A, vitamin A derivatives, vitamin E, vitamin E derivatives, BHT, and combinations thereof.

Optionally the body or face care composition comprises from 0.001 wt.-% to 5.0 wt.-%, preferably from 0.01 wt.-% to 3.0 wt.-%, even more preferably from 0.1 wt.-% to 2.0 wt.-% of at least one biogenic active substance. Biogenic active substances are listed above. In at least one embodiment, the biogenic active substance is selected from the group consisting of aloe vera extract, collagen hydrolysates, bisabolol, vitamin C, vitamin E, allantoin, vitamin B5, tocopherol acetate, retinyl palmitate, and combinations thereof.

Optionally the body or face care composition comprises from 0.01 wt.-% to 4.0 wt.-%, preferably from 0.1 wt.-% to 3.0 wt.-%, even more preferably from 0.4 wt.-% to 1.0 wt.-% of at least one preservative or preservation boosting ingredient. Preservatives or preservation boosting ingredients are listed above. In at least one embodiment, the preservative or preservation boosting ingredient is selected from the group consisting of methylparben, phenoxyethanol, DMDM hydantoin, ethylhexylglycerin, sodium benzoate, potassium sorbate, levulinic acid, p-anisic acid, sorbitan caprylate, and combinations thereof.

Optionally the body or face care composition comprises from 0.01 wt.-% to 3.0 wt.-%, preferably from 0.05 wt.-% to 2.0 wt.-%, even more preferably from 0.1 wt.-% to 1.0 wt.-% of at least one perfume or fragrance ingredient. Perfume or fragrance ingredients or are listed above.

Optionally the body or face care composition comprises from 0.01 wt.-% to 20 wt.-%, preferably from 0.1 wt.-% to 10 wt.-%, even more preferably from 0.5 wt.-% to 5.0 wt.-% of at least one further auxiliary. Auxiliaries are listed above.

In a preferred embodiment, the body or face care composition has a pH value from 2.0 to 10.0, preferably from 3.0 to 9.0, even more preferably from 4.0 to 8.0 and very preferably from 5.0 to 7.0.

In at least one embodiment, the composition is a cleansing composition such as body washes, face washes, micellar waters or gels, body scrubs, face peeling, facial exfoliators, liquid soaps, bath additives, bubble baths, shower creams or milks, shower foams and face masks. Optionally the cleansing composition comprises from 0.5 wt.-% to 25 wt.-%, preferably from 1.0 wt.-% to 20 wt.-%, even more preferably from 2.0 wt.-% to 15 wt.-% of at least one surfactant. Surfactants are listed above. In at least one embodiment, the surfactant is selected from the group consisting of sodium laureth sulfate, sodium lauryl sulfate, ammonium lauryl sulfate, sodium lauroyl sarcosinate, sodium methyl cocoyl taurate, cocamidopropyl betaine, sodium cocoyl glutamate, lauryl glucoside, cocoyl methyl glucamide, and combinations thereof.

Optionally the cleansing composition comprises from 0.01 wt.-% to 15 wt.-%, preferably from 0.1 wt.-% to 10 wt.-%, even more preferably from 0.5 wt.-% to 5.0 wt.-% of at least one viscosity modifier or thickening agent. Viscosity modifier or thickening agents are listed above. In at least one embodiment, the viscosity modifier or thickening agent is selected from the group consisting of carbomers, acrylates copolymers, xanthan gum, laureth-3 or 4, cocamide DEA, coco glucosides, stearyl alcohol, and combinations thereof.

Optionally the cleansing composition comprises from 0.01 wt.-% to 15 wt.-%, preferably from 0.05 wt.-% to 10 wt.-%, even more preferably from 0.5 wt.-% to 5.0 wt.-% of at least one particulate substance. Particulate substances are listed above. In at least one embodiment, the particulate substance is selected from the group consisting of silica, mica, bentonite, kaolin, talc, polyethylene, clay, and combinations thereof.

Optionally the cleansing composition comprises from 0.001 wt.-% to 30 wt.-%, preferably from 0.05 wt.-% to 20 wt.-%, even more preferably from 0.1 wt.-% to 10 wt.-% of at least one oily substance. Oily substances are listed above. In at least one embodiment, the oily substance is selected from the group consisting of sweet almond oil, caprylic/capric triglycerides, dimethicone, mineral oil, squalane, castor oil, isopropyl isostearate, jojoba oil, dicaprylyl carbonate, isohexadecane, $C_{12}$-$C_{15}$ alkyl benzoate, and combinations thereof.

Optionally the cleansing composition comprises from 0.05 wt.-% to 15 wt.-%, preferably from 0.1 wt.-% to 10 wt.-%, even more preferably from 0.5 wt.-% to 5.0 wt.-% of at least one functional acid or/and an active ingredient. Functional acids or/and an active ingredients are listed above. In at least one embodiment, the functional acid or/and an active ingredient is selected from the group consisting of alpha- and beta-hydroxy acids, lactic acid, glycolic acid, salicylic acid, citric acid, vitamin C derivatives, proteolytic enzymes, and combinations thereof.

Optionally the cleansing composition comprises from 0.001 wt.-% to 5.0 wt.-%, preferably from 0.05 wt.-% to 3.0 wt.-%, even more preferably from 0.1 wt.-% to 1.0 wt.-% of at least one electrolyte. Electrolytes are listed above. In at least one embodiment, the electrolyte is selected from the group consisting of sodium chloride, magnesium chloride, sodium citrate, sodium acetate, and combinations thereof.

Optionally the cleansing composition comprises from 0.01 wt.-% to 5.0 wt.-%, preferably from 0.1 wt.-% to 3.0 wt.-%, even more preferably from 0.4 wt.-% to 1.0 wt.-% of at least one preservative or preservation boosting ingredient. Preservatives or preservation boosting ingredients are listed above. In at least one embodiment, the preservative or preservation boosting ingredient is selected from the group consisting of sodium benzoate, methylisothiazolinone, benzoic acid, methylparben, phenoxyethanol, DMDM hydantoin, potassium sorbate, and combinations thereof.

Optionally the cleansing composition comprises from 0.01 wt.-% to 20 wt.-%, preferably from 0.1 wt.-% to 10 wt.-%, even more preferably from 0.5 wt.-% to 5.0 wt.-% of at least one further auxiliary. Auxiliaries are listed above.

In a preferred embodiment, the cleansing composition has a pH value from 2.0 to 10.0, preferably from 3.0 to 8.0, even more preferably from 4.0 to 7.0.

In at least one embodiment, the composition is a sun care composition such as sun sprays, sun milks, sun lotions, sun gels. Body and face care compositions with sun protection agents and/or UV filters such as day creams, hand creams, foundations, lip balms and face serums can also serve as sun care compositions. Optionally the sun care composition comprises from 0.1 wt.-% to 15 wt.-%, preferably from 0.5 wt.-% to 10 wt.-%, even more preferably from 1.0 wt.-% to 5.0 wt.-% of at least one emulsifier, coemulsifier and/or solubilizer. Emulsifiers, coemulsifiers and/or solubilizers are listed above. In at least one embodiment, the emulsifier, coemulsifier and/or solubilizer is selected from the group consisting of glyceryl stearate, cetearyl alcohol, polysorbate 20, stearic acid, cetearyl glucoside, PEG-40 hydrogenated castor oil, cetyl phosphate, steareth-2, ceteth-10 phosphate, trilaureth-4 phosphate, polyglyceryl-2 sesquiisostearate, cetyl PEG/PPG-10/1 dimethicone, and combinations thereof.

Optionally the sun care composition comprises from 0.001 wt.-% to 50 wt.-%, preferably from 0.05 wt.-% to 40 wt.-%, even more preferably from 0.1 wt.-% to 30 wt.-% of at least one oily substance. Oily substances are listed above. In at least one embodiment, the oily substance is selected from the group consisting of sweet almond oil, caprylic/capric triglycerides, dimethicone, mineral oil, squalane, castor oil, isopropyl isostearate, jojoba oil, dicaprylyl carbonate, cyclopentasiloxane, isohexadecane, $C_{12}$-$C_{15}$ alkyl benzoate, and combinations thereof.

Optionally the sun care composition comprises from 0.001 wt.-% to 30 wt.-%, preferably from 0.05 wt.-% to 20 wt.-%, even more preferably from 0.1 wt.-% to 10 wt.-%, most preferably from 0.05 wt.-% to 5.0 wt.-% of at least one sun protection agent and/or UV filter. Sun protection agents and/or UV filters are listed above. In at least one embodiment, the sun protection agent and/or UV filter is selected from the group consisting of 2-ethylhexyl 4-methoxycinnamate, methyl methoxycinnamate, 2-ethylhexyl salicylate, 2-ethylhexyl-2-cyano-3,3-diphenyl-2-propenoate, 2-hydroxy-4-methoxybenzophenone-5-sulfonic acid, polyethoxylated p-aminobenzoates, and combinations thereof.

Optionally the sun care composition comprises from 0.1 wt.-% to 10 wt.-%, preferably from 0.5 wt.-% to 7.5 wt.-%, even more preferably from 1.0 wt.-% to 5.0 wt.-% of at least one film former. Film formers are listed above. In at least one embodiment, the film former is selected from the group consisting of VP/eicosene copolymer, acrylates/octylacrylamide copolymer, VP/VA copolymer, styrene/acrylates copolymer, acrylates copolymer, butyl ester of PVM/MA copolymer, hydroxyethylcellulose, polypropylsilsesquioxane, polyurethane-64, acrylates/polytrimethylsiloxymethacrylate copolymer, and combinations thereof.

Optionally the sun care composition comprises from 0.01 wt.-% to 5.0 wt.-%, preferably from 0.1 wt.-% to 3.0 wt.-%, even more preferably from 0.4 wt.-% to 1.0 wt.-% of at least one preservative or preservation boosting ingredient. Preservatives or preservation boosting ingredients are listed above. In at least one embodiment, the preservative or preservation boosting ingredient is selected from the group consisting of methylparben, phenoxyethanol, DMDM hydantoin, ethylhexylglycerin, sodium benzoate, potassium sorbate, sorbitan caprylate, and combinations thereof.

Optionally the sun care composition comprises from 0.01 wt.-% to 20 wt.-%, preferably from 0.1 wt.-% to 10 wt.-%, even more preferably from 0.5 wt.-% to 5.0 wt.-% of at least one further auxiliary. Auxiliaries are listed above. In a preferred embodiment, the sun care composition has a pH value from 3.0 to 9.0, preferably from 4.0 to 8.0, even more preferably from 5.0 to 7.0.

In at least one embodiment, the composition is a face toner. Optionally the face toner composition comprises from 0.001 wt.-% to 5.0 wt.-%, preferably from 0.05 wt.-% to 3.0 wt.-%, even more preferably from 0.1 wt.-% to 1.0 wt.-% of at least one skin conditioning agent. Skin conditioning agents are listed above. In at least one embodiment, the skin conditioning agent is selected from the group consisting of glycerin, urea, hydroxyethyl urea, allantoin, bisabolol, panthenol, and combinations thereof.

Optionally the face toner composition comprises from 0.01 wt.-% to 15 wt.-%, preferably from 0.1 wt.-% to 10 wt.-%, even more preferably from 0.5 wt.-% to 5.0 wt.-% of at least one viscosity modifier or thickening agent. Viscosity modifier or thickening agents are listed above. In at least one embodiment, the viscosity modifier or thickening agent is selected from the group consisting of carbomers, acrylates copolymers, xanthan gum, carrageenan, and combinations thereof.

Optionally the face toner composition comprises from 0.01 wt.-% to 5.0 wt.-%, preferably from 0.1 wt.-% to 3.0 wt.-%, even more preferably from 0.4 wt.-% to 1.0 wt.-% of at least one preservative or preservation boosting ingredient. Preservatives or preservation boosting ingredients are listed above. In at least one embodiment, the preservative or preservation boosting ingredient is selected from the group consisting of methylparaben, phenoxyethanol, methylisothiazolinone, ethylhexylglycerin, and combinations thereof.

Optionally the face toner composition comprises from 0.01 wt.-% to 20 wt.-%, preferably from 0.1 wt.-% to 10.0 wt.-%, even more preferably from 0.5 wt.-% to 5.0 wt.-% of at least one further auxiliary. Auxiliaries are listed above.

In a preferred embodiment, the face toner composition has a pH value from 3.0 to 9.0, preferably from 4.0 to 8.0, even more preferably from 5.0 to 7.0.

In at least one embodiment, the composition is a bar soap or syndet composition. Optionally the bar soap or syndet composition comprises from 1.0 wt.-% to 50 wt.-%, preferably from 2.0 wt.-% to 30 wt.-%, even more preferably from 5.0 wt.-% to 20 wt.-% of at least one surfactant. Surfactants are listed above. In at least one embodiment, the surfactant is selected from the group consisting of disodium lauryl sulfosuccinate, sodium palm kernelate, sodium palmate, sodium cocoate, sodium tallowate, palm kernel acid, sodium cocoyl isethionate, sodium isethionate, sodium lauryl sulfate, cocamidopropyl betaine, and combinations thereof.

Optionally the bar soap or syndet composition comprises from 0.01 wt.-% to 20 wt.-%, preferably from 0.05 wt.-% to 15 wt.-%, even more preferably from 0.5 wt.-% to 10 wt.-% of at least one particulate substance. Particulate substances are listed above. In at least one embodiment, the particulate substance is selected from the group consisting of silica, calcium carbonate, sodium bicarbonate, titanium dioxide, polyethylene, and combinations thereof.

Optionally the bar soap or syndet composition comprises from 0.001 wt.-% to 5.0 wt.-%, preferably from 0.05 wt.-% to 3.0 wt.-%, even more preferably from 0.1 wt.-% to 1.0 wt.-% of at least one electrolyte. Electrolytes are listed above. In at least one embodiment, the electrolyte is selected from the group consisting of sodium chloride, magnesium chloride, sodium citrate, sodium acetate, and combinations thereof.

Optionally the bar soap or syndet composition comprises from 0.01 wt.-% to 20 wt.-%, preferably from 0.1 wt.-% to 10 wt.-%, even more preferably from 0.5 wt.-% to 5.0 wt.-% of at least one further auxiliary. Auxiliaries are listed above.

In a preferred embodiment, the bar soap or syndet composition has a pH value from 3.0 to 13.0, preferably from 4.0 to 12.0, even more preferably from 5.0 to 10.0.

In at least one embodiment, the composition is a composition suitable for wet wipes. Optionally the composition suitable for wet wipes comprises from 0.1 wt.-% to 10 wt.-%, preferably from 0.3 wt.-% to 5.0 wt.-%, even more preferably from 0.5 wt.-% to 3.0 wt.-% of at least one emulsifier, coemulsifier and/or solubilizer. Emulsifiers, coemulsifiers and/or solubilizers are listed above. In at least one embodiment, the emulsifier, coemulsifier and/or solubilizer is selected from the group consisting of glyceryl stearate, cetearyl alcohol, polysorbate 20, stearic acid, cetearyl glucoside, PEG-40 hydrogenated castor oil, and combinations thereof.

Optionally the composition suitable for wet wipes comprises from 0.001 wt.-% to 30 wt.-%, preferably from 0.05 wt.-% to 20 wt.-%, even more preferably from 0.1 wt.-% to 10 wt.-% of at least one oily substance. Oily substances are listed above. In at least one embodiment, the oily substance is selected from the group consisting of caprylic/capric triglycerides, dimethicone, mineral oil, squalane, castor oil, isopropyl isostearate, jojoba oil, isohexadecane, $C_{12}$-$C_{15}$ alkyl benzoate, and combinations thereof.

Optionally the composition suitable for wet wipes comprises from 0.01 wt.-% to 5.0 wt.-%, preferably from 0.1 wt.-% to 3.0 wt.-%, even more preferably from 0.4 wt.-% to 1.0 wt.-% of at least one preservative or preservation boosting ingredient. Preservatives or preservation boosting ingredients are listed above. In at least one embodiment, the preservative or preservation boosting ingredient is selected from the group consisting of methylparaben, phenoxyethanol, sodium benzoate, potassium sorbate, benzoic acid, ethylhexylglycerin, sorbitan caprylate, and combinations thereof.

Optionally composition suitable for wet wipes comprises from 0.01 wt.-% to 20 wt.-%, preferably from 0.1 wt.-% to 10 wt.-%, even more preferably from 0.5 wt.-% to 5.0 wt.-% of at least one further auxiliary. Auxiliaries are listed above.

In a preferred embodiment, the composition suitable for wet wipes has a pH value from 2.0 to 10, preferably from 3.0 to 9.0, even more preferably from 4.0 to 8.0.

In at least one embodiment, the composition is a deodorizing and/or antiperspirant composition. In at least one embodiment, the composition is in the form of a cream, a roll-on, a solid, an aerosol or a gel. Optionally the deodorizing and/or antiperspirant composition comprises from 0.001 wt.-% to 10 wt.-%, or from 0.01 wt.-% to 9.0 wt.-%, or from 0.05 wt.-% to 8.0 wt.-%, or from 0.1 wt.-% to 5.0 wt.-% of at least one antiperspirant and/or deodorizing agent. Antiperspirants and deodorizing agents are listed above. In at least one embodiment, the antiperspirant and/or deodorizing agent is selected from the group consisting of aluminium chlorohydrate, allantoin, bisabolol, aluminium chloride, magnesium zirconium complexes or aluminum zirconium chloride hydroxide, and combinations thereof.

Optionally the deodorizing and/or antiperspirant composition comprises 0.01 wt.-% to 3.0 wt.-%, preferably from 0.05 wt.-% to 2.0 wt.-%, even more preferably from 0.1 wt.-% to 1.0 wt.-% of at least one perfume or fragrance ingredient. Perfume or fragrance ingredients or are listed above. In at least one embodiment, the perfume or fragrance ingredient is selected from the group consisting of linalool, limonene, geraniol, coumarin, butylphenyl methylpropional, alpha-isomethyl ionone, citral, hexyl cinnamal, and combinations thereof.

Optionally the deodorizing and/or antiperspirant composition comprises from 0.5 wt.-% to 60 wt.-%, preferably from 1.0 wt.-% to 50 wt.-%, even more preferably from 2.0 wt.-% to 40 wt.-% of at least one propellant. Propellants are listed above. In at least one embodiment, the propellant is selected from the group consisting of nitrogen, carbon dioxide, pentane, n-butane, iso-butane, propane, and combinations thereof.

Optionally the deodorizing and/or antiperspirant composition comprises from 0.01 wt.-% to 20 wt.-%, preferably from 0.1 wt.-% to 10 wt.-%, even more preferably from 0.5 wt.-% to 5.0 wt.-% of at least one further auxiliary. Auxiliaries are listed above.

In a preferred embodiment, the deodorizing and/or antiperspirant composition has a pH value from 2.0 to 8.0, preferably from 3.0 to 7.0, even more preferably from 4.0 to 6.0.

In at least one embodiment, the composition is a shaving composition. Optionally the shaving composition comprises from 0.1 wt.-% to 10 wt.-%, preferably from 0.3 wt.-% to 5.0 wt.-%, even more preferably from 0.5 wt.-% to 3.0 wt.-% of at least one emulsifier, coemulsifier and/or solubilizer. Emulsifiers, coemulsifiers and/or solubilizers are listed above. In at least one embodiment, the emulsifier, coemulsifier and/or solubilizer is selected from the group consisting of cetearyl alcohol, polysorbate 20, palmitic acid, laureth-23, stearic acid, cetearyl glucoside, PEG-40 hydrogenated castor oil, and combinations thereof.

Optionally the shaving composition comprises from 0.001 wt.-% to 5.0 wt.-%, preferably from 0.05 wt.-% to 3.0 wt.-%, even more preferably from 0.1 wt.-% to 1.0 wt.-% of at least one skin conditioning agent. Skin conditioning agents are listed above. In at least one embodiment, the skin conditioning agent is selected from the group consisting of glycerin, urea, sorbitol, aloe vera leaf juice, and combinations thereof Optionally the shaving composition comprises from 0.5 wt.-% to 60 wt.-%, preferably from 1.0 wt.-% to 50 wt.-%, even more preferably from 2.0 wt.-% to 40 wt.-% of at least one propellant. Propellants are listed above. In at least one embodiment, the propellant is selected from the group consisting of nitrogen, carbon dioxide, pentane, n-butane, iso-butane, propane, and combinations thereof.

Optionally the shaving composition comprises from 0.1 wt.-% to 20 wt.-%, preferably from 0.3 wt.-% to 10 wt.-%, even more preferably from 0.5 wt.-% to 5.0 wt.-% of at least one surfactant. Surfactants are listed above. In at least one embodiment, the surfactant is selected from the group consisting of sodium laureth sulfate, sodium lauryl sulfate, ammonium lauryl sulfate, sodium lauroyl sarcosinate, cocamidopropyl betaine, and combinations thereof.

Optionally the shaving composition comprises from 0.01 wt.-% to 20 wt.-%, preferably from 0.1 wt.-% to 10 wt.-%, even more preferably from 0.5 wt.-% to 5.0 wt.-% of at least one further auxiliary. Auxiliaries are listed above.

In at least one embodiment, the cosmetic, dermatological or pharmaceutical composition is for use on hair and/or scalp. In at least one embodiment, the composition is an emulsion or gel, preferably an oil-in-water (o/w), cream gel, hydro-alcoholic gel or hydrogel composition. In a preferred embodiment, the hair care composition has a viscosity from 100 000 to 150 000 mPa·s, preferably from 1 000 to 100 000 mPa·s, more preferably from 2 000 to 50 000 mPa·s and very preferably from 5 000 to 30 000 mPa·s (25° C., Brookfield RVT, T-C spindle at 20 revolutions per minute).

In at least one embodiment, the composition is a shampoo composition. Optionally the shampoo composition comprises from 0.5 wt.-% to 30 wt.-%, preferably from 1.0 wt.-% to 15 wt.-%, even more preferably from 2.0 wt.-% to 10 wt.-% of at least one surfactant. Surfactants are listed above. In at least one embodiment, the surfactant is selected from the group consisting of sodium laureth sulfate, sodium lauryl sulfate, ammonium lauryl sulfate, sodium lauroyl sarcosinate, sodium methyl cocoyl taurate, cocamidopropyl betaine, sodium cocoyl glutamate, lauryl glucoside, cocoyl methyl glucamide, and combinations thereof.

Optionally the shampoo composition comprises from 0.1 wt.-% to 10 wt.-%, preferably from 0.5 wt.-% to 7.5 wt.-%, even more preferably from 1.0 wt.-% to 5.0 wt.-% of at least one cationic polymer. Cationic polymers are listed above. In at least one embodiment, the cationic polymer is selected from the group consisting of polyquaternium-10, guar hydroxypropyltrimonium chloride, polyquaternium-7, polyquaternium-6, and combinations thereof.

Optionally the shampoo composition comprises from 0.1 wt.-% to 15 wt.-%, preferably from 0.5 wt.-% to 10 wt.-%, even more preferably from 1.0 wt.-% to 5.0 wt.-% of at least one pearlizing agent. Pearlizing agents are listed above. In at least one embodiment, the cationic polymer is selected from the group consisting of ethylene glycol distearates and/or polyethylene glycol distearates with 3 glycol units on average, and combinations thereof.

Optionally the shampoo composition comprises from 0.001 wt.-% to 5.0 wt.-%, preferably from 0.05 wt.-% to 3.0 wt.-%, even more preferably from 0.1 wt.-% to 1.0 wt.-% of at least one electrolyte. Electrolytes are listed above. In at least one embodiment, the electrolyte is selected from the group consisting of sodium chloride, magnesium chloride, sodium citrate, sodium acetate, and combinations thereof.

Optionally the shampoo composition comprises from 0.01 wt.-% to 15 wt.-%, preferably from 0.1 wt.-% to 10 wt.-%, even more preferably from 0.5 wt.-% to 5.0 wt.-% of at least one viscosity modifier or thickening agent. Viscosity modifier or thickening agents are listed above. In at least one embodiment, the viscosity modifier or thickening agent is selected from the group consisting of carbomers, acrylates copolymers, xanthan gum, laureth-3 or 4, cocamide DEA, coco glucosides, stearyl alcohol, and combinations thereof.

Optionally the shampoo composition comprises from 0.01 wt.-% to 5.0 wt.-%, preferably from 0.1 wt.-% to 3.0 wt.-%, even more preferably from 0.4 wt.-% to 1.0 wt.-% of at least one preservative or preservation boosting ingredient. Preservatives or preservation boosting ingredients are listed above.

Optionally the shampoo composition comprises from 0.01 wt.-% to 20 wt.-%, preferably from 0.1 wt.-% to 10 wt.-%, even more preferably from 0.5 wt.-% to 5.0 wt.-% of at least one further auxiliary. Auxiliaries are listed above.

In at least one embodiment, the composition is a hair conditioning and/or hair and/or scalp treatment composition such as leave-in and rinse-off conditioners, masks, lotions, combing creams, detangling creams, anti-frizz liquids, hair serums, scalp serums, color protection creams.

Optionally the hair conditioning and/or hair and/or scalp treatment composition comprises from 0.1 wt.-% to 15 wt.-%, preferably from 0.5 wt.-% to 10 wt.-%, even more preferably from 1.0 wt.-% to 5.0 wt.-% of at least one emulsifier, coemulsifier and/or solubilizer. Emulsifiers, coemulsifiers and/or solubilizers are listed above. In at least one embodiment, the emulsifier, coemulsifier and/or solubilizer is selected from the group consisting of cetearyl alcohol, cetrimonium chloride, behentrimonium chloride, steartrimonium chloride, cetyl alcohol, stearyl alcohol, stearic acid, isostearamidopropyl dimethylamine, and combinations thereof.

Optionally the hair conditioning and/or hair and/or scalp treatment composition comprises from 0.01 wt.-% to 20 wt.-%, preferably from 0.05 wt.-% to 10 wt.-%, even more preferably from 0.1 wt.-% to 5.0 wt.-% of at least one oily substance. Oily substances are listed above. In at least one embodiment, the oily substance is selected from the group consisting of dimethicone, squalene, amodimethicone, argan oil, jojoba oil, cyclopentasiloxane, mineral oil, castor oil, shea butter, and combinations thereof.

Optionally the hair conditioning and/or hair and/or scalp treatment composition comprises from 0.1 wt.-% to 10 wt.-%, preferably from 0.5 wt.-% to 7.5 wt.-%, even more preferably from 1.0 wt.-% to 5.0 wt.-% of at least one cationic polymer. Cationic polymers are listed above. In at least one embodiment, the cationic polymer is selected from the group consisting of polyquaternium-10, guar hydroxypropyltrimonium chloride, polyquaternium-7, polyquaternium-6, and combinations thereof.

Optionally the hair conditioning and/or hair and/or scalp treatment composition comprises from 0.001 wt.-% to 5.0 wt.-%, preferably from 0.01 wt.-% to 3.0 wt.-%, even more preferably from 0.1 wt.-% to 2.0 wt.-% of at least one biogenic active substance. Biogenic active substances are listed above. In at least one embodiment, the biogenic active substance is selected from the group aloe collagen hydrolysates, bisabolol, allantoin, hydrolyzed wheat protein, hydrolyzed silk, hydrolyzed keratin, amino acids and its derivatives, glycoproteins, and combinations thereof.

Optionally the hair conditioning and/or hair and/or scalp treatment composition comprises from 0.01 wt.-% to 5.0 wt.-%, preferably from 0.1 wt.-% to 3.0 wt.-%, even more preferably from 0.4 wt.-% to 1.0 wt.-% of at least one preservative or preservation boosting ingredient. Preservatives or preservation boosting ingredients are listed above. In at least one embodiment, the preservative or preservation boosting ingredient is selected from the group consisting of sodium benzoate, methylparaben, phenoxyethanol, methylisothiazolinone, DMDM hydantoin, methylchloroisothiazolinone, zinc pyrithione, and combinations thereof.

Optionally the hair conditioning and/or hair and/or scalp treatment composition comprises from 0.01 wt.-% to 20 wt.-%, preferably from 0.1 wt.-% to 10 wt.-%, even more preferably from 0.5 wt.-% to 5.0 wt.-% of at least one further auxiliary. Auxiliaries are listed above In at least one embodiment, the composition is a hair styling composition such as mousses, gels, sprays and waxes.

Optionally the hair styling composition comprises from 0.1 wt.-% to 10 wt.-%, preferably from 0.5 wt.-% to 7.5 wt.-%, even more preferably from 1.0 wt.-% to 5.0 wt.-% of at least one film former. Film formers are listed above. In at least one embodiment, the film former is selected from the group consisting of PVP, VP/VA copolymer, styrene/acrylates copolymer, acrylates copolymer, butyl ester of PVM/MA copolymer, hydroxyethylcellulose, chitosan, polyquaternium-10, polypropylsilsesquioxane, polyurethane-64, and combinations thereof.

Optionally the hair styling composition comprises from 0.1 wt.-% to 10 wt.-%, preferably from 0.5 wt.-% to 7.5 wt.-%, even more preferably from 1.0 wt.-% to 5.0 wt.-% of at least one cationic polymer. Cationic polymers are listed above. In at least one embodiment, the cationic polymer is selected from the group consisting of polyquaternium-10, guar hydroxypropyltrimonium chloride, polyquaternium-7, polyquaternium-6, and combinations thereof.

Optionally the hair styling composition comprises from 0.5 wt.-% to 60 wt.-%, preferably from 1.0 wt.-% to 50 wt.-%, even more preferably from 2.0 wt.-% to 40 wt.-% of at least one propellant. Propellants are listed above. In at least one embodiment, the propellant is selected from the group consisting of nitrogen, carbon dioxide, pentane, n-butane, iso-butane, propane, and combinations thereof.

Optionally the hair styling composition comprises from 0.01 wt.-% to 5.0 wt.-%, preferably from 0.1 wt.-% to 3.0 wt.-%, even more preferably from 0.4 wt.-% to 1.0 wt.-% of at least one preservative or preservation boosting ingredient. Preservatives or preservation boosting ingredients are listed above. In at least one embodiment, the preservative or preservation boosting ingredient is selected from the group consisting of sodium benzoate, methylparaben, phenoxyethanol, methylisothiazolinone, DMDM hydantoin, methylchloroisothiazolinone, zinc pyrithione, and combinations thereof.

Optionally the hair styling composition comprises from 0.01 wt.-% to 20 wt.-%, preferably from 0.1 wt.-% to 10.0 wt.-%, even more preferably from 0.5 wt.-% to 5.0 wt.-% of at least one further auxiliary. Auxiliaries are listed above In at least one embodiment, the composition is a mouthwash composition. Optionally mouthwash composition comprises from 0.001 wt.-% to 3.0 wt.-%, preferably from 0.01 wt.-% to 2.0 wt.-%, even more preferably from 0.05 wt.-% to 1.0 wt.-% of at least one flavouring agent. Flavouring agents are listed above. In at least one embodiment, the flavouring agent is selected from the group consisting of stevioside, xylite, sodium saccharin, sorbitol, methyl salicylate, menthol, eucalyptol, thymol, and combinations thereof.

Optionally the mouthwash composition comprises from 0.1 wt.-% to 6.0 wt.-%, preferably from 0.2 wt.-% to 4.0 wt.-%, even more preferably from 0.3 wt.-% to 2.0 wt.-% of at least one solubilizer. Solubilizers are listed above. In at least one embodiment, the solubilizer is selected from the group consisting of PEG-40 hydrogenated castor oil, polysorbate 20, poloxamer 407, and combinations thereof.

Optionally the mouthwash composition comprises from 0.001 wt.-% to 5.0 wt.-%, preferably from 0.05 wt.-% to 3.0 wt.-%, even more preferably from 0.1 wt.-% to 1.0 wt.-% of at least one electrolyte. Electrolytes are listed above. In at least one embodiment, the electrolyte is selected from the group consisting of sodium fluoride, sodium monofluorophosphate, stannous fluoride, and combinations thereof.

Optionally the mouthwash composition comprises from 0.01 wt.-% to 5.0 wt.-%, preferably from 0.1 wt.-% to 3.0 wt.-%, even more preferably from 0.4 wt.-% to 1.0 wt.-% of at least one preservative or preservation boosting ingredient. Preservatives or preservation boosting ingredients are listed above. In at least one embodiment, the preservative or preservation boosting ingredient is selected from the group consisting of sodium benzoate, benzoic acid, chlorhexidine, and combinations thereof.

Optionally the mouthwash composition comprises from 0.01 wt.-% to 20 wt.-%, preferably from 0.1 wt.-% to 10 wt.-%, even more preferably from 0.5 wt.-% to 5.0 wt.-% of at least one further auxiliary. Auxiliaries are listed above. In a preferred embodiment, the mouthwash composition has a pH value from 2.0 to 10.0, preferably from 3.0 to 9.0, even more preferably from 4.0 to 8.0.

Fifth Aspect

A fifth aspect relates to a method for treating hair and/or skin comprising applying the composition according to the fourth aspect onto hair and/or skin.

Sixth Aspect

A sixth aspect relates to a container comprising a package comprising a receptacle comprising the composition according to the fourth aspect and wherein the package comprises a closure for containing the composition in the receptacle.

Seventh Aspect

A seventh aspect relates to the use of a lower alcohol the synthesising a product according to the second aspect. In at least one embodiment, the product relates to the compound according to Formula (2). In at least one embodiment, the lower alcohol contains less than six carbon atoms. In at least one embodiment, the lower alcohol contains only one OH group. In at least one embodiment, the lower alcohol is selected from the group consisting of ethanol, methanol and mixtures thereof. In at least one embodiment, the lower alcohol is used as a solvent.

EXAMPLES

The examples which follow are intended to illustrate the subject matter of the invention, though without restricting it thereto.

Example Process

Synthesis Example 1

100 g Piroctone Olamine are placed in a 4-necked 500 mL round bottomed flask and subsequently 93.3 mL ethanol are added and stirring is started. 74.2 mL hydrochloric acid are added. After 5 min., inside temperature has risen to 32° C., the starting material is not completely dissolved. The suspension is heated at 50° C. The inside temperature reaches 50° C., the solution becomes clear. After 1.5 h heating, the solution is allowed to cool to room temperature and is poured onto 300 mL ice water. The resulting precipitate is filtered over a Hirsch funnel and washed with water. The remaining solid is tried at 100° C. over night yielding 78.9 g (99.1%) of 1-hydroxy-4-methyl-6-(2,4,4-trimethylpentyl)-2(1H)-pyridone.

Synthesis Example 2

100 g Piroctone Olamine are placed in a 4-necked 500 mL round bottomed flask and subsequently. 93.3 mL methanol are added and stirring is started. 74.2 mL hydrochloric acid are added. After 5 min., inside temperature has risen to 32° C., the starting material is not completely dissolved. The suspension is heated at 50° C. The inside temperature reaches 50° C., the solution becomes clear. After 1.5 h heating, the solution is allowed to cool to room temperature and is poured onto 300 mL ice water. The resulting precipitate is filtered over a Hirsch funnel and washed with water. The remaining solid is tried at 100° C. over night yielding 77.89 g (97.9%) 1-hydroxy-4-methyl-6-(2,4,4-trimethylpentyl)-2(1H)-pyridone.

The Piroctone Olamine in the above syntheses can be swapped for the following compounds according to Formula (1):

| Compound according to Formula (1) | Resulting compound according to Formula (2) |
|---|---|
| 6-[{4-(4-chlorophenoxy)-phenoxy}methyl]-1-hydroxy-4-methyl-2-pyridone monoethanol amine salt | 6-[{4-(4-chlorophenoxy)-phenoxy}methyl]-1-hydroxy-4-methyl-2-pyridone |
| 4-methyl-6-(cyclohexyl)-1-hydroxy-2-pyridone monoethanol amine salt | 4-methyl-6-(cyclohexyl)-1-hydroxy-2-pyridone |
| 4-methyl-6-pentyl-pyran-2-one monoethanol amine salt | 4-Methyl-6-pentyl-pyran-2-one |

Example Compositions

KEY FOR ALL EXAMPLES: [1]=4-methyl-6-(2,4,4-trimethylpentyl)-1-hydroxy-2-pyridone (i.e. a compound according to Formula (2)).

Example 1: Facial Toner

| | |
|---|---|
| Piroctone [1] | 0.10 |
| Ethanol | 25.00 |
| Propylene Glycol | 5.00 |
| Iso-adipate | 0.20 |
| Fragrance | 0.30 |
| Preservative | QS |
| Allantoin | 0.10 |
| Hammamelis | 5.00 |
| D-panthenol | 0.50 |
| Water | QSP |
| Total | 100% |

Example 2: Styling Gel

| A | Piroctone [1] | 0.06 |
|---|---|---|
|   | Ethanol | 30.00 |
| C | IPVP/VA Copolymer [3] | 2.00 |
| D | Coceth-10 | 0.40 |
|   | Fragrance | 0.20 |
| E | Dye | QSP |
| F | Carbomer [4] | 1.00 |
| G | Preservative | QS |
| B | Caustic soda 10% solution | 2.60 |
| B | Water | QSP |
|   | Total | 100% |

KEY: [3] = Luviscol VA 641; [4] = Carbopol 980.

Procedure for Formulating Example 2:
I Dissolve the components of A.
II Mix the components of D.
III Add I to II and stir.
IV Add C to III.
V Dissolve F in B while stirring.
VI Add IV to V while stirring.
VII Add the components of E to VI.
VIII Finally adjust the pH with G.

Example 3: Liquid Soap

| A | Piroctone [1] | 0.25 |
|---|---|---|
| B | Water | 10.00 |
| C | Sodium Laureth Sulfate | 10.00 |
| D | Fragrance | 0.20 |
|   | PEG-7 Glyceryl Cocoate | 2.00 |
|   | Water | QSP |
|   | Cocoamido propyl betaine | 2.00 |
|   | Sodium Chloride | 1.20 |
|   | Total | 100% |

Procedure for Formulating Example 3:
I Mix A with B.
II Add C and stir until the solution is clear.
III Add the components of D.
IV If necessary adjust the pH, then adjust the viscosity with E

Example 4: Anti-Dandruff Shampoo

| A | Piroctone [1] | 0.40 |
|---|---|---|
| B | Water | 10.00 |
| C | Sodium Laureth Sulfate | 10.00 |
| D | Sodium Cocoyl Glutamate | 1.25 |
|   | Fragrance | 0.30 |
| E | Polyquaternium 10 | 0.30 |
| F | Water | QSP |
|   | Cocamidopropyl Betaine | 2.40 |
|   | Laureth-3 | 1.50 |
| G | Sodium Chloride | 1.50 |
|   | Total | 100% |

Procedure for Formulating Example 4:
I Mix A with B.
II Add C to I and keep stirring until a clear solution has been obtained.
III Stir the components of Done after another into I.
IV Dissolve E in F under stirring while heating slightly and then stir into I.
V Stir the components of G another into I
VI If necessary adjust the pH.
VII Finally adjust the viscosity with H.

Example 5: Day Cream

| A | Hostacerin EWO* | 16.00 |
|---|---|---|
|   | Isopropyl Palmitate | 6.00 |
|   | Squalane | 4.00 |
|   | Avocado Oil | 2.00 |
|   | Caprylic/Capric Triglyceride | 4.00 |
|   | Piroctone [1] | 0.40 |
| B | Water | QSP |
|   | Glycerine | 4.00 |
|   | Magnesium Sulfate•7H2O | 0.70 |
|   | Sodium Chloride | 1.50 |
| C | Fragrance | 0.20 |
|   | Tocopheryl Acetate |   |
|   | Total | 100% |

KEY: *= Polyglyceryl-2 Sesquiisostearate (and) Ethylhexyl Stearate (and) Simmondsia Chinensis (Jojoba) Seed Oil (and) Beeswax (Cera Alba) (and) Magnesium Stearate (and) Aluminum Tristearate (and) Copernicia Cerifera (Caranuba) Wax Procedure for Formulating Example 5:
I Melt A at 80° C. (add preservative after heating phase).
II Heat Bat 80° C. (add preservative after heating phase).
III Stir II into I and stir with a high shear mixer until cool.
IV Add C to III at 35° C.

Example 6: Anti-Dandruff Shampoo

| A | Piroctone [1] | 0.30 |
|---|---|---|
|   | Water | 20.00 |
|   | Sodium C14-17 Alkyl sec. Sulfonate [2] | 4.80 |
|   | Sodium Cocoyl Glutamate | 2.90 |
|   | Cocamide MIPA [5] | 2.00 |
|   | Glucotain Flex [6] | 2.00 |
| B | Fragrance | 0.30 |
| C | Water | QSP |
|   | Glycerin | 2.00 |
|   | Sorbitol | 1.00 |
|   | Panthenol | 0.50 |
| D | Cocoamidopropyl Betaine | 4.50 |
| E | Preservative | QS |
|   | Total | 100% |

KEY: [2] = Hostapur SAS 60; [5] = Rewomid IPP 240; [6] = Lauroyl/Myristoyl Methyl Glucamide Procedure for Formulating Example 6
I Dissolve A while stirring and heating to approx. 50° C.
II Stir B in I at approx. 35° C.
III Add the components of C and stir until a clear solution has been obtained
IV Stir the components of D into II
V Add E to III
VI Adjust the pH to 5.5-6.0 with citric acid Example Method of Using Example 6:

Example 6 is applied to wet hair in an amount of about 5-10 mL per head (dry weight). Tap water is employed to create a lather and spread the composition throughout the hair and scalp. The composition is immediately rinsed from the hair. The hair may further be conditioned.

EXPERIMENTAL

Experiment 1: Solubility Testing

A compound according to Formula (2), namely 1-hydroxy-4-methyl-6-(2,4,4-trimethylpentyl)-2(1H)-pyridone, is tested for solubility in various solvents. A 10% (w/w) solution of this compound is tested. The solubility is tested directly after addition as well as after being left to stand for a week. The results of these experiments are found in the below table.

| Solvent | Solubility | Comments |
|---|---|---|
| Ethanol | yes | Dissolves slowly leading to a clear slightly yellowish solution. |
| Isopropanol | no | Not completely dissolved, supernatant solution is yellowish. |
| tert. Butanol (2.5% $H_2O$) | no | Dissolves only partially and separates rapidely to a white precipitate and a clear solution. |
| Methanol | yes | Soluble. Resulting soltuion is clear. |
| Acetone (purity >99%) | no | Dissolves to a large extend. Supernatant is yellowish |
| 3-Pentanone | no | Not completely soluble, supernatant solution is yellowish. |
| 1,3-Dioxolane | no | Not soluble. |
| 2-Methyltetrahydrofuran | no | Not soluble. |

Conclusion from Experiment 1:

Ethanol and methanol are able to solubilize 1-hydroxy-4-methyl-6-(2,4,4-trimethylpentyl)-2(1H)-pyridone excellently.

Experiment 2: Efficacy

A compound according to Formula (2), namely 1-hydroxy-4-methyl-6-(2,4,4-trimethyl pentyl)-2(1H)-pyridone (named as Piroctone in the below table), is tested for efficacy versus various microbes. Comparison is made versus Piroctone Olamine (=Octopirox®).

| Microbiology MIC in ppm pH 6.5 (*Malassezia* Agar) | Octopirox (5% in butylpolyglycol) | Piroctone (3.98% in butylpolyglycol) | Octopirox (5%) + Velsan SC (50%) in butylpolyglycol | Piroctone (3.98%) + Velsan SC (50%) in butylpolyglycol |
|---|---|---|---|---|
| *Malassezia furfur* DSM 6170 | 500 | 500 | 500 | 500 |
| *Malassezia pachydermatis* DSM 6172 | 500 | 500 | 500 | 500 |
| *Malassezia globosa* ATCC 4889 | 500 | 500 | 500 | 500 |
| *Candida albicans* DSM 1386 | 500 | 500 | 500 | 500 |
| *Saccharomyces cerevisiae* DSM 70449 | 500 | 500 | 500 | 500 |

Conclusion from Experiment 2:

Piroctone shows the same activity in MIC tests at a lower concentration than Piroctone Olamine.

What is claimed is:

1. A process comprising the steps of:
   (a) providing a solution comprising:
      (i) at least one solvent, wherein the solvent is selected from the group consisting of ethanol, methanol, and mixtures thereof;
      (ii) at least one acid;
      (iii) at least one compound according to Formula (1)

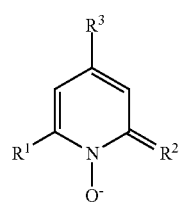

(1)

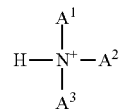

wherein $R^1$ is selected from the group consisting of H, a non-substituted or halogen-substituted, branched or unbranched $C_1$-$C_{20}$-alkyl radical, a non-substituted or halogen-substituted $C_5$-$C_8$-cycloalkyl radical, a non-substituted or halogen-substituted $C_8$-$C_{10}$-aryl radical or a non-substituted or halogen-substituted, branched or unbranched $C_7$-$C_{20}$-aralkyl radical;

$R^2$ is either O or S, $R^3$ is H or a branched or unbranched $C_1$-$C_4$-alkyl radical;

$A^1$ is selected from the group consisting of H, a non-substituted halogen-substituted, branched or unbranched $C_1$-$C_{20}$-alkyl radical, a non-substituted or halogen-substituted $C_5$-$C_8$-cycloalkyl radical, a branched or unbranched hydroxylated $C_1$-$C_{20}$-alkyl radical;

A² is selected from the group consisting of H, a non-substituted halogen-substituted, branched or unbranched $C_1$-$C_{20}$-alkyl radical, a non-substituted or halogen-substituted $C_5$-$C_8$-cycloalkyl radical, a branched or unbranched hydroxylated $C_1$-$C_{20}$-alkyl radical;

A³ is selected from the group consisting of H, a non-substituted halogen-substituted, branched or unbranched $C_1$-$C_{20}$-alkyl radical, a non-substituted or halogen-substituted $C_5$-$C_8$-cycloalkyl radical, a branched or unbranched hydroxylated $C_1$-$C_{20}$-alkyl radical;

(b) heating the solution to at least 35° C.; and
(c) recovering a compound according to Formula (2)

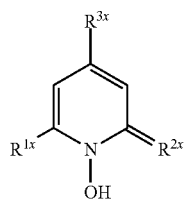

(2)

wherein $R^{1x}$ is selected from the group consisting of H, an unsubstituted or halogen-substituted, branched or unbranched $C_1$-$C_{20}$-alkyl radical, an unsubstituted or halogen-substituted $C_5$-$C_8$-cycloalkyl radical, an unsubstituted or halogen-substituted $C_8$-$C_{10}$-aryl radical or an unsubstituted or halogen-substituted, branched or unbranched $C_7$-$C_{20}$-aralkyl radical;

$R^{2x}$ is either O or S, $R^{3x}$ is H or a branched or unbranched $C_1$-$C_4$-alkyl radical.

2. The process according to claim 1, wherein the molar ratio of the compound according to Formula (1) to the acid is from 1:1 to 1:5.

3. The process according to claim 1, wherein the solution is prepared by mixing at least one compound according to Formula (1) with the at least one solvent, followed by gradually adding the at least one acid.

4. The process according to claim 1, wherein during step (b), the compound according to Formula (1) is dissolved in the solution.

5. The process according to claim 1, wherein the cation in Formula (1) is selected from the group consisting of monoethanolamine, diethanolamine, triethanolamine, methylamine, dimethylamine, trimethylamine, ethyl amine, diethylamine, trimethylamine, diisopropylethylamine, and combinations thereof.

6. The process according to claim 1, wherein the acid is selected from the group consisting of hydrochloric acid, hydrobromic acid, hydroiodic acid, sulfuric acid, $HNO_3$, acetic acid, formic acid, and mixtures thereof.

7. The process according to claim 1, wherein in step (b) the solution is heated to a temperature of between 35° C. and 80° C.

8. The process according to claim 1, wherein the weight ratio of compound according to Formula (1) to the solvent is from 1:0.7 to 1:1.3.

9. The process according to claim 1, wherein in step (b) the solution is heated for at least 30 minutes.

10. The process according to claim 1, wherein step (c) comprises cooling the solution.

11. The process according to claim 1, wherein $R^2$ and $R^{2x}$ are both O.

12. The process according to claim 1, wherein $R^3$ and $R^{3x}$ are methyl and $R^1$ and $R^{1x}$ are either cyclohexyl or 2,4,4-trimethylpentyl.

13. The process according to claim 1, wherein the compound according to Formula (1) is selected from the group consisting of a monoethanolamine salt of 4-methyl-6-(2,4,4-trimethylpentyl) hydroxy-2-pyridone and a diethanolamine salt of 4-methyl-6-(2,4,4-trimethylpentyl)-1-hydroxy-2-pyridone.

14. The process according to claim 1, wherein the compound according to Formula (2) is selected from the group consisting of 2-hydroxypyridine-1-oxide and 1-hydroxy-4-methyl-6-(2,4,4-trimethylpentyl)-2(1H)-pyridone.

15. The process according to claim 1, wherein the cation in Formula (1) is selected from the group consisting of monoethanolamine, diethanolamine, and combinations thereof.

16. The process according to claim 1, wherein step (c) comprises pouring the solution onto ice, filtering off solid material, and subsequently drying the solid material.

* * * * *